(12) United States Patent
Okuda et al.

(10) Patent No.: US 9,241,507 B2
(45) Date of Patent: Jan. 26, 2016

(54) **REDUCING AGENT FROM MICROORGANISM BELONGING TO GENUS *BACILLUS* AND APPLICATION FOR SAME**

(71) Applicant: Amano Enzyme Inc., Nagoya-shi (JP)

(72) Inventors: Keita Okuda, Kakamigahara (JP); Shotaro Yamaguchi, Kakamigahara (JP)

(73) Assignee: Amano Enzyme Inc., Nagoya-shi (JP)

( * ) Notice: Subject to any disclaimer, the term of this patent is extended or adjusted under 35 U.S.C. 154(b) by 63 days.

(21) Appl. No.: 14/048,538

(22) Filed: Oct. 8, 2013

(65) Prior Publication Data

US 2014/0037791 A1    Feb. 6, 2014

Related U.S. Application Data

(60) Division of application No. 13/696,446, which is a continuation of application No. PCT/JP2011/060622, filed on May 9, 2011, now abandoned.

(30) Foreign Application Priority Data

May 12, 2010  (JP) ................ 2010-109779

(51) Int. Cl.
| | | |
|---|---|---|
| A23L 1/31 | (2006.01) | |
| C12N 9/02 | (2006.01) | |
| C12P 21/06 | (2006.01) | |
| C07H 21/04 | (2006.01) | |
| C07K 1/00 | (2006.01) | |
| A23L 1/272 | (2006.01) | |
| A23L 1/314 | (2006.01) | |
| A61K 35/74 | (2015.01) | |
| A23L 1/30 | (2006.01) | |
| A23L 1/27 | (2006.01) | |
| C12N 9/04 | (2006.01) | |
| A61K 35/00 | (2006.01) | |

(52) U.S. Cl.
CPC . *A23L 1/272* (2013.01); *A23L 1/27* (2013.01); *A23L 1/30* (2013.01); *A23L 1/3002* (2013.01); *A23L 1/3149* (2013.01); *A61K 35/74* (2013.01); *C12N 9/0004* (2013.01); *C12N 9/0006* (2013.01); *C12N 9/0051* (2013.01); *C12Y 101/01284* (2013.01); *C12Y 108/01004* (2013.01); *A61K 2035/11* (2013.01)

(58) Field of Classification Search
CPC ....... A23L 1/3149; A23L 1/3002; A23L 1/27; A23L 1/30; A23L 1/272; A61K 35/74; A61K 2035/11; C12N 9/0004; C12N 9/0006; C12N 9/0051; C12Y 101/01284; C12Y 108/01004
USPC ............ 426/59, 56; 435/189, 69.1; 536/23.2; 530/350
See application file for complete search history.

(56) References Cited

FOREIGN PATENT DOCUMENTS

| EP | 1676489 A2 | 7/2006 |
|---|---|---|
| JP | 2002-536015 A | 10/2002 |
| JP | 2003-018976 A | 1/2003 |
| JP | 2005-087058 A | 4/2005 |
| JP | 2005-508614 A | 4/2005 |
| JP | 2006-056908 A | 3/2006 |
| JP | 2006-061016 A | 3/2006 |
| JP | 2006-166815 A | 6/2006 |
| JP | 2008-228702 A | 10/2008 |
| JP | 2009-165445 A | 7/2009 |
| WO | WO-00/47725 A1 | 8/2000 |
| WO | WO-03/004608 A2 | 1/2003 |
| WO | WO-2005-097486 A1 | 10/2005 |

OTHER PUBLICATIONS

Anlezark et al., Bacillus amyloliquefaciens orthologue of Bacillus subtilis ywrO encodes a nirtoreductase enzyme which activates the prodrug CB 1954. Microbiology, 2002, vol. 148: 297-306.*

Ockerman et al., Microbiological growth and pH effects on bovine tissue inoculated with Pseudomonas putrefaciens, Bacillus subtilis, or Leuconostoc mesenterroides. J. Food Sci., 1997, vol. 42: 141-145.*

Abir U. Igamberdiev et al., "Dihydrolipoamide dehydrogenase from porcine heart catalyzes NADH-dependent scavenging of nitric oxide," FEBS Letters 568, 2004, pp. 146-150.

Office Action dated Nov. 2, 2014, issued for the Chinese patent application No. 201180023168.9.

Arihara et al., "Conversation of Metmyoglobin to Bright Red Myoglobin Derivatives by *Chromobacterium violaceum*, *Kurthia* sp., and *Lactobacillus fermentum* JCM1173," *J. Food Science*, vol. 58, No. 1, 1993, pp. 38-42.

Arihara et al., "Nyusankin no Nikushoku Seigyo Kino—Lactobacillus-zoku Oyobi Enterococus-zoku Nyusankin ni yoru Sensekishoku Myoglobin Yudotai no Keisei," Shokuniku-no-kagaku, vol. 35, No. 1, 1994, pp. 159-162 and an information sheet.

Barbe et al, Definition: "dihydrolipoamide dehydrogenase [*Bacillus subtilis slubsp. Subtilis str.* 168]," Database DDBJ/EMBL/GenBank [online], Accession No. NP389344, Mar. 31, 2010 uploaded, 3 pages.

Hemila et al., "Secretory S Complex of *Bacillus subtilis*: Sequence Analysis and Identity to Pyruvate Dehydrogenase," *J. Bacteriology*, vol. 172, No. 9, 1990, pp. 5052-5063.

Imahori et al., "Dihydro-Lipoamide Dehydrogenase" Seikagaku-jiten Tokyo Kagaku Dojin, 2002, p. 663 and an information sheet.

International Search Report dated Jun. 14, 2011, issued for PCT/JP2011/060622.

European Search Report dated Jun. 25, 2015, issued for Application PCT/JP2011/060622.

* cited by examiner

*Primary Examiner* — Ganapathirama Raghu
(74) *Attorney, Agent, or Firm* — Locke Lord LLP

(57) ABSTRACT

The present invention is intended to provide a reducing agent effective for color development of meat and uses therefor. The present invention provides a reducing agent containing a heme reductase derived from a microorganism belonging to the genus *Bacillus*. Preferably, crushed bacterial cells of *Bacillus subtilis*, *Bacillus amyloliquefaciens*, *Bacillus natto*, *Bacillus thuringiensis*, or *Bacillus mycoides* are used.

11 Claims, 38 Drawing Sheets

FIG. 8

|  | DEAE. Fr.61-63 | Hydroxyapatite 2-Fr.19 | Gel filtration 2-Fr.13 | Gel filtration 2-Fr.14 | Gel filtration 2-Fr.15 |
|---|---|---|---|---|---|
| u/mL | 1.36 | 0.78 | 0.10 | 0.32 | 0.14 |
| Protein content (mg/mL) | 2.8454 | 0.1057 | 0.0665 | 0.0390 | 0.0142 |
| u/mg | 0.48 | 7.39 | 1.56 | 8.16 | 9.94 |

FIG. 37

Reactivity for potassium ferricyanide

|      | Km(mM)        | kcat/Km(M$^{-1}$min$^{-1}$) |
|------|---------------|------------------------------|
| DLD  | 0.323         | $8.22 \times 10^5$           |
| yodC | 0.174±0.012   | $(2.17±0.14) \times 10^6$    |

FIG. 38

Reactivity for myoglobin

|  | Km($\mu$M) | kcat/Km($M^{-1}min^{-1}$) |
|---|---|---|
| DLD | 57.2 | $5.99 \times 10^4$ |
| yodC | 7.58±1.81 | $(1.30 \pm 0.90) \times 10^6$ |

REDUCING AGENT FROM MICROORGANISM BELONGING TO GENUS *BACILLUS* AND APPLICATION FOR SAME

CROSS-REFERENCE TO RELATED APPLICATIONS

This application is a Divisional of U.S. Ser. No. 13/696,446, filed Nov. 6, 2012 and published as U.S. 2013-0058911A1 on Mar. 7, 2013. U.S. Ser. No. 13/696,446 is the U.S. national phase, pursuant to 35 U.S.C. §371, of PCT international application Ser. No. PCT/JP2011/060622, filed May 9, 2011, designating the United States and published in Japanese on Nov. 17, 2011 as publication WO 2011/142300. PCT/JP2011/060622 claims priority to Japanese Patent Application No. 2010-109779, filed May 12, 2010. The entire contents of the aforementioned patent applications are incorporated herein by reference.

SEQUENCE LISTING

The instant application contains a Sequence Listing which has been submitted in ASCII format via EFS-Web and is hereby incorporated by reference in its entirety. Said ASCII copy, created on Oct. 8, 2013, is named 91674DIV305882_ST25.txt and is 12,288 bytes in size.

TECHNICAL FIELD

The present invention relates to a reducing agent derived from a microorganism belonging to the genus *Bacillus* and uses thereof. The reducing agent of the present invention is particularly useful for improving the color tone of meat or processed meat. The present application claims priority based on Japanese Patent Application No. 2010-109779 filed on May 12, 2010, and the content of the patent application is hereby incorporated by reference herein in its entirety.

BACKGROUND ART

Meat color is an important factor for consumers to evaluate the meat quality. Bright red meat is regarded as good quality, and brown meat is regarded as stale. In this manner, the meat color markedly influences the consumers' willing to buy the meat and their evaluation of the meat.

The color tone of meat reflects the proportion of myoglobin derivatives in the meat. Once myoglobin is oxidized to metmyoglobin, the color tone changes into brown, and thus the commercial value of the meat product markedly decreases.

In order to prevent browning of meat, processed meat such as ham and sausage is generally treated with a color development agent such as a nitrate or nitrite. However, since nitrates and nitrites have acute toxicity to cause methemogulobinemia in human, their usage is limited to 70 ppm or less in terms of the residual nitrite. In addition, it is said that nitrous acid can react with a secondary amine to form nitrosamine which is a carcinogen. Therefore, from the viewpoint of safety, color developing substances and color development methods which replace color development agents such as nitrates or nitrites have been searched. For example, a method for preventing browning through the addition of raffinose (see Patent Document 1), a method for preventing browning through the addition of a *Flammulina veluptipes* extract (see Patent Document 2), and a method for developing a color through the use of components contained in vegetables (see Patent Document 3) were found. However, the methods described in Patent Documents 1 and 2 cannot achieve sufficient color development effect, and the method described in Patent Document 3 uses nitrates contained in vegetables, and thus has a problem with safety.

In addition, Patent Document 4 proposes the method of maintaining the color tone of meat by substituting iron in myoglobin with zinc to form a zinc myoglobin-protoporphin IX complex, and Patent Documents 5 and 6 propose the methods of maintaining the fresh red color of meat by accelerating the formation of a zinc myoglobin-protoporphin IX complex through the use of ferrochelatase or yeast. These methods cannot act on metmyoglobin which has been generated, and cannot achieve sufficient color development effect or color tone holding effect.

PRIOR ART DOCUMENT

Patent Documents

Patent Document 1
Japanese Unexamined Patent Application Publication No. 2003-18976
Patent Document 2
Japanese Unexamined Patent Application Publication No. 2008-228702
Patent Document 3
Japanese Unexamined Patent Application Publication No. 2009-165445
Patent Document 4
Japanese Unexamined Patent Application Publication No. 2006-56908
Patent Document 5
Japanese Unexamined Patent Application Publication No. 2005-87058
Patent Document 6
Japanese Unexamined Patent Application Publication No. 2006-61016

SUMMARY OF THE INVENTION

Problems to be Solved by the Invention

The present invention is intended to provide a reducing agent which is effective for improving the color tone of meat or processed meat and uses thereof (for example, color tone improvement method without using a color development agent such as a nitrite).

Means for Solving the Problem

In order to find substances which improve the color tone of meat, the inventors carried out screening mainly on microorganisms belonging to the genus *Bacillus*. As a result of screening, a microorganism strain producing substances with high meat color development effect was identified. As a result of further study, the substances which are expected to be highly useful were found to exhibit reduction activity on metmyoglobin. More specifically, the microorganism belonging to the genus *Bacillus* produces the substances accelerating the development of meat color by metmyoglobin reduction activity. The substances exhibit reduction action on heme, and are useful in developing meat color, and also in the applications where the reduction of heme or heme protein is effective or necessary. For example, the substances may be used for the purpose of reducing methemoglobin which has a structure similar to metmyoglobin.

As a result of further study, the substances derived from the microorganism belonging to the genus *Bacillus* (substances exhibiting reduction action) were found to be dihydrolipoyl dehydrogenase and nitroreductase.

The present invention has been accomplished based on the above results, and includes the following aspects.

[1] A reducing agent containing a heme reductase derived from a microorganism belonging to the genus *Bacillus*.

[2] The reducing agent of [1], wherein the heme is the heme of metmyoglobin.

[3] The reducing agent of [1], wherein the heme is the heme of methemoglobin.

[4] The reducing agent of any one of [1] to [3], which is composed of crushed bacterial cells of a microorganism belonging to the genus *Bacillus*.

[5] The reducing agent of any one of [1] to [4], wherein the microorganism belonging to the genus *Bacillus* is a microorganism selected from the group consisting of *Bacillus subtilis*, *Bacillus amyloliquefaciens*, *Bacillus natto*, *Bacillus thuringiensis*, and *Bacillus mycoides*.

[6] The reducing agent of [1], wherein the heme reductase is dihydrolipoyl dehydrogenase or nitroreductase.

[7] The reducing agent of [1], which contains dihydrolipoyl dehydrogenase and nitroreductase as the heme reductases.

[8] The reducing agent of [6] or [7], wherein the amino acid sequence of the dihydrolipoyl dehydrogenase includes the amino acid sequence of SEQ ID NO: 3, and the amino acid sequence of the nitroreductase includes the amino acid sequence of SEQ ID NO: 12.

[9] The reducing agent of any one of [6] to [8], wherein the dihydrolipoyl dehydrogenase and nitroreductase are recombinant proteins.

[10] A color tone improver composed of the reducing agent of any one of [1] to [9].

[11] A color tone improver composed of the reducing agent of any one of [1] to [9] and a substance which substitutes iron in the heme group of myoglobin with zinc.

[12] The color tone improver of [11], wherein the substance is ferrochelatase.

[13] The color tone improver of any one of [10] to [12], which is used for improving the color tone of meat or processed meat.

[14] A color tone improver for meat or processed meat containing dihydrolipoyl dehydrogenase and/or nitroreductase.

[15] The color tone improver of any one of [10] to [14], which improves the color tone by color development action, color development acceleration action, and/or color fading preventive action.

[16] A medicine containing the reducing agent of any one of [1] to [9].

[17] The medicine of [16], which is an oral preparation.

[18] The medicine of [16], which is a parenteral preparation.

[19] A method for producing a reducing agent including the following steps (1) and (2):
(1) a step of culturing a microorganism belonging to the genus *Bacillus* producing a heme reductase under conditions suitable for the production of the enzyme; and
(2) a step of recovering the enzyme from the culture.

[20] The production method of [19], wherein the step (2) includes the following steps:
(2-1) a step of collecting bacterial cells from the culture; and
(2-2) a step of preparing crushed bacterial cells.

[21] The production method of [19] or [20], wherein the heme is the heme of metmyoglobin.

[22] The production method of [19] or [20], wherein the heme is the heme of methemoglobin.

[23] The production method of any one of [19] to [22], wherein the microorganism belonging to the genus *Bacillus* is selected from the group consisting *Bacillus subtilis*, *Bacillus amyloliquefaciens*, *Bacillus natto*, *Bacillus thuringiensis* and *Bacillus mycoides*.

[24] A color tone improvement method, including subjecting meat or processed meat to the action of the color tone improver of any one of [10] to [15].

[25] A color tone improvement method, including subjecting meat or processed meat to the action of crushed bacterial cells of a microorganism belonging to the genus *Bacillus* selected from the group consisting of *Bacillus subtilis*, *Bacillus amyloliquefaciens*, *Bacillus natto*, *Bacillus thuringiensis*, and *Bacillus mycoides*.

[26] A prophylactic or therapeutic method using the reducing agent of any one of [1] to [9] for a disease associated with or caused by one or more clinical conditions or symptoms selected from blood circulation disorder and hypoxia or hypoxemia.

BRIEF DESCRIPTION OF THE DRAWINGS

FIG. 8 shows the comparison of specific activity of the samples obtained during purification.

FIG. 37 shows the comparison of reactivity of DLD and yodC to potassium ferricyanide.

FIG. 38 shows the comparison of reactivity of DLD and yodC to myoglobin.

DESCRIPTION OF EMBODIMENTS

Terms

Figure 1:
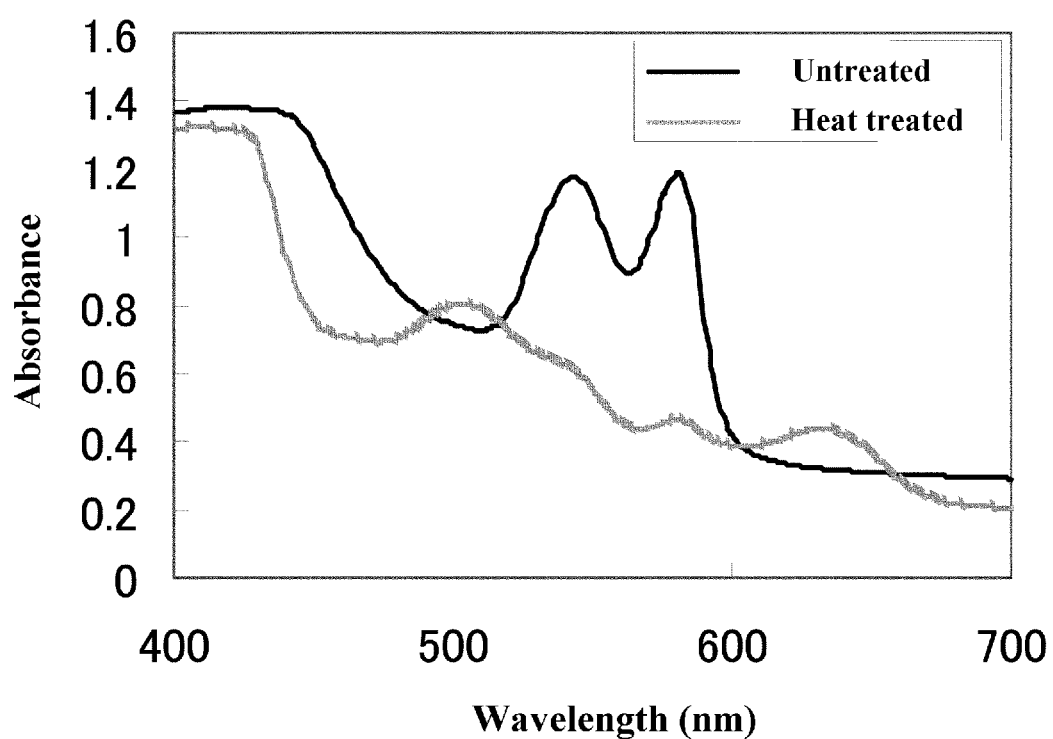
FIG. 1 shows the absorption spectra of the solutions containing the crushed bacterial cell extract of a microorganism belonging to the genus *Bacillus* (or its heat treated extract) and freeze-dried ham powder.

In the present description, the term "heme" means a complex composed of an iron atom and porphyrin (iron-porphyrin complex). The term "heme protein" is the generic name of protein including heme. The term "heme reductase" means a protein exhibiting reduction activity to the iron atom in heme. The degree of the activity is not particularly limited. Typically, a heme reductase exhibits activity reducing the metho compound of heme protein. With the focus on the activity, heme reductase may be called heme protein reductase.

In the present description, "metmyoglobin reductase" refers to a protein exhibiting activity reducing metmyoglobin, which is a myoglobin derivative. The intensity (degree) of the activity is not particularly limited. Accordingly, even if reduction activity of an enzyme on metmyoglobin is weaker than other activity of the enzyme, the enzyme is included in the "metmyoglobin reductase" referred herein.

In the present description, "color tone improver" refers to a substance or composition used for the improvement of "color tone", the formation of which is contributed by a metalloporphyrin complex. Examples of the metalloporphyrin complex include a copper porphyrin complex, a cobalt porphyrin complex, and an iron porphyrin complex. But the metalloporphyrin complex is not limited to these examples, as long as the metal in the complex can be reduced. Preferred examples of the metalloporphyrin complex include an iron porphyrin complex, and examples of the composition containing the iron porphyrin complex include heme protein. Examples of the composition rich in heme protein include meat or processed meat.

The color tone improver of the present invention improves the color tone of the target by color development action, color development acceleration action, and/or color fading prevention action. For example, the color tone improver of the present invention can reduce the metal in a metalloporphyrin complex to improve the color tone. Alternatively, the color tone improver can prevent oxidation of a dye composed of a metalloporphyrin complex to maintain the color tone of the dye, and thus improve the color tone. A preferred target for which the color tone improver of the present invention is used is meat or processed meat. More specifically, according to a preferred embodiment, the color tone improver of the present invention is used to color development, color tone maintenance, or color fading prevention of meat or processed meat. The term "color development of meat" means the development of a red color tone characteristic to meat or processed meat.

1. Reducing Agent Derived from the Genus *Bacillus*

A first aspect of the present invention relates to a reducing agent. The reducing agent of the present invention includes a heme reductase produced by *Bacillus* as an active ingredient. As shown by the below-described examples, as a result of the large-scale screening by the inventors, it was found that *Bacillus subtilis, Bacillus amyloliquefaciens, Bacillus natto, Bacillus thuringiensis*, and *Bacillus mycoides*, which are microorganisms belonging to the genus *Bacillus*, produce polypeptides having high metmyoglobin reduction activity. On the basis of this finding, a preferred embodiment of the present invention uses a metmyoglobin reductase produced by any of these microorganisms. These microorganisms are available from, for example, public storage institutions such as NBRC (Biological Resource Center, National Institute of Technology and Evaluation), JCM (RIKEN BioResource Center), and ATCC (American Type Culture Collection). *Bacillus natto* is commercially and readily available. In addition, *Bacillus natto* is available from Miyagino *Bacillus Natto* Manufacturer.

The reducing agent of the present invention contains the active ingredient (polypeptide), and may further contain, for example, an excipient, a buffering agent, a suspending agent, a stabilizer, a pH controlling agent, a preservative, an antiseptic, a perfume, a thickener, an oil or fat, a brightener, a binder, a binding reinforcer, an emulsification stabilizer, or a normal saline solution. Examples of the excipient include starch, dextrin, maltose, trehalose, lactose, D-glucose, sorbitol, D-mannitol, white sugar, and glycerol. Examples of the buffering agent include phosphates, citrates, and acetates. Examples of the stabilizer include propylene glycol and ascorbic acid. Examples of the pH controlling agent include organic acids such as itaconic acid, succinic acid, tartaric acid, fumaric acid, citric acid, malic acid, adipic acid, gluconic acid, pyrophosphoric acid, acetic acid, lactic acid, α-ketoglutaric acid, and phytic acid, and salts of these organic acids; inorganic acids and salts of inorganic acids such as carbonates; acidic amino acids such as aspartic acid and glutamic acid; and basic amino acids such as arginine, lysine, and histidine. Examples of the preservative include phenol, benzalkonium chloride, benzyl alcohol, chlorobutanol, and methylparaben. Examples of the antiseptic include ethanol, benzalkonium chloride, paraoxybenzoic acid, and chlorobutanol. Examples of the perfume include animal perfumes such as musk, civet, castoreum, and ambergris; vegetable perfumes such as anise essential oil, angelica essential oil, ylang ylang essential oil, iris essential oil, fennel essential oil, orange essential oil, Cananga essential oil, caraway essential oil, cardamom essential oil, guaiacum essential oil, cumin essential oil, Lindera umbellata essential oil, cinnamon essential oil, cinnamon essential oil, geranium essential oil, copaiba balsam essential oil, coriander essential oil, *perilla* essential oil, cedarwood essential oil, citronella essential oil, jasmine essential oil, ginger glass essential oil, cedar essential oil, spearmint essential oil, peppermint essential oil, star anise essential oil, tuberose essential oil, clove essential oil, neroli essential oil, wintergreen essential oil, tolu balsam essential oil, patchouli essential oil, rose essential oil, palmarosa essential oil, Japanese cypress essential oil, hiba essential oil, sandal wood essential oil, petitgrain essential oil, bay laurel essential oil, vetiver essential oil, bergamot essential oil, Peru balsam essential oil, bois de rose essential oil, linalool essential oil, mandarin essential oil, eucalyptus essential oil, lime essential oil, lavender essential oil, linaloe essential oil, lemon glass essential oil, lemon essential oil, rosemary essential oil, and Japanese peppermint essential oil; and other synthetic perfumes. Examples of the thickener include natural polymer or starch or cellulose natural polymer derivatives. Examples of the natural polymer include seaweed extracts such as fucoidan and carrageenan, seed extracts such as guar gum, resin-like slimes such as gum arabic, and microorganism-produced slimes such as xanthan gum. Examples of the starch or cellulose natural polymer derivatives include starch-based (for example, starch phosphate) or cellulose-based (for example, methyl cellulose-based) natural polymer derivatives. Examples of the oil and fat include avocado oil, linseed oil, almond oil, fennel oil, *perilla* oil, olive oil, orange oil, orange roughy oil, cacao butter, camomile oil, carrot oil, cucumber oil, coconut oil, sesame oil, rice oil, safflower oil, shea butter, liquid shea butter, soybean oil, camellia oil, corn oil, rapeseed oil, persic oil, castor oil, sunflower oil, grape seed oil, cottonseed oil, peanut oil, turtle oil, mink oil, egg yolk oil, palm oil, palm kernel oil, *Rhus* succedanea fruit wax, coconut oil, beef tallow, and lard. These oils and fats may be modified by, for example, hydrogenation, fractionation, or interesterification. Examples of the brightener include waxes (vegetable or animal) such as beeswax, carnauba wax, whale wax, lanolin, liquid state lanolin, reduced lanolin, hard lanolin, candelilla wax, montan wax, shellac wax, rice wax, squalene, squalane, and pristane; and mineral oils such as liquid paraffin, vaseline, paraffin, ozokerite, ceresin, and microcrystalline wax. Examples of the binder include soybean protein, egg protein, milk protein, blood protein, casein, starch, and transglutaminase. Examples of the binding reinforcer include polymerized phosphates. Examples of the emulsification stabilizer include casein sodium. Examples of the other additive include natural fatty acids such as lauric acid, myristic acid, palmitic acid, stearic acid, behenic acid, oleic acid, linoleic acid, linolenic acid, docosahexaenoic acid, eicosapentaenoic acid, 1,2-hydroxy stearic acid, undecylenic acid, tall oil, and lanolin fatty acid; and synthetic fatty acids such as isononanoic acid, caproic acid, 2-ethyl butanoic acid, isopentane acid, 2-methylpentanoic acid, 2-ethyl hexanoic acid, and isopentanoic acid.

According to an embodiment, the reducing agent of the present invention is composed of crushed bacterial cells of the microorganism according to the present invention which produces polypeptide. More specifically, the reducing agent according to this embodiment contains the crushed bacterial cells of the specified microorganism. A crushed bacterial cell solution (normally obtained by a procedure including culture of the microorganism, collection of the microorganism, and crushing of the bacterial cells) may be used as the crushed bacterial cells. Alternatively, the crushed bacterial cell solution may be subjected to further treatment (for example, purification treatment, freezing treatment, drying treatment, or addition of other components) before the use as crushed bacterial cells.

As a result of the study by the inventors, it was found that the active ingredients derived from a microorganism belonging to the genus *Bacillus* (substances exhibiting reduction action, and effective particularly at improving the color tone of meat) are dihydrolipoyl dehydrogenase (DLD) and nitroreductase (yodC) (see the below-described examples). Therefore, one aspect of the present invention provides a reducing agent containing dihydrolipoyl dehydrogenase or nitroreductase derived from a microorganism belonging to the genus *Bacillus* as heme reductase. According to a preferred embodiment, the reducing agent contains both of dihydrolipoyl dehydrogenase and nitroreductase. The amino acid sequence of dihydrolipoyl dehydrogenase is shown in SEQ ID NO: 3, and that of nitroreductase is shown in SEQ ID NO: 12.

The identification of effective heme reductases and identification of their amino acid sequences have allowed the use of enzymes prepared by a genetic engineering method. Therefore, one aspect of the present invention uses an enzyme which has been prepared by a genetic engineering method, more specifically a heme reductase composed of a recombinant protein. Specifically, a reducing agent containing recombinant dihydrolipoyl dehydrogenase and/or recombinant nitroreductase as active ingredients is provided. Recombinant protein refers to an artificially prepared protein by a gene recombination technique.

2. Applications of Reducing Agent

A second aspect of the present invention relates to the applications of the reducing agent of the present invention.

The applications provided by the present invention are broadly divided into the improvement of the color tone and other uses. The former application, more specifically the use as a color tone improver is particularly important. The targets of color tone improvement by the present invention are those involved with a metalloporphyrin complex in the formation of the color tone. Preferred examples of the target include meat and processed meat. The color tone of meat reflects the proportion of the myoglobin derivatives contained in the meat. As described above, the reducing agent of the present invention contains a heme reductase (preferably metmyoglobin reductase) as an active ingredient. Accordingly, when the reducing agent of the present invention is allowed to act on meat, metmyoglobin in the meat is reduced to form reduced myoglobin. The reduced myoglobin is oxygenated to be converted to oxymyoglobin which shows a bright red color tone. Upon the action of the reducing agent of the present invention, the metmyoglobin level in meat or processed meat decreases, and at the same time oxymyoglobin is formed, which results in the improvement of the color tone. In addition, the oxidation of reduced myoglobin or oxymyoglobin is prevented, and as a result of this, color fading of the meat is prevented. In this manner, the reducing agent of the present invention will exhibit the effects of color development and color tone maintenance, or prevention of color fading. The target of the color fading prevention effect is a metalloporphyrin complex, and the complex is not particularly limited as long as the metal in the complex is oxidizable. A preferred metalloporphyrin complex is an iron porphyrin complex. Accordingly, a preferred target of the color fading prevention effect is a heme protein containing an iron porphyrin complex. Most preferred targets are reduced myoglobin or oxymyoglobin, and meat or processed meat containing reduced myoglobin and/or oxymyoglobin.

When the reducing agent of the present invention is used for the color tone improvement of meat or processed meat (more specifically, the color tone improvement method using the reducing agent of the present invention as a color tone improver), meat or processed meat is treated by the reducing agent of the present invention. The treatment conditions are set to be generally suitable for the action of the metmyoglobin reductase composing the reducing agent (preferably optimal conditions). The preferred treatment conditions are readily specified based on the preliminary experiment using the meat or processed meat to be treated. Specific examples of the treatment method (the use of a solution of crushed bacterial cells for the improvement of meat color tone). Firstly, a solution of crushed bacterial cells of a certain microorganism (a microorganism belonging to the genus *Bacillus* producing metmyoglobin reductase) is prepared, and its pH is adjusted to about 5.5, thereby reproducing the pH in meat. Subsequently, meat is exposed to the solution at 4° C. The exposure is usually achieved by injection of a suspension into block meat, followed by tumbling, or blending of minced meat with a suspension. When the exposure is achieved appropriately, the suspension thoroughly penetrates into meat. The treatment temperature may be near 40° C. for developing a color, but is preferably 4° C. or near 4° C. in consideration of meat quality.

The type of meat to be treated is not limited. As described above, the color tone of meat reflects the proportion of the myoglobin derivatives contained in meat. The reducing agent of the present invention influences the proportion of the myoglobin derivatives in meat, and accelerates the color development. Accordingly, the present invention is applicable to meat or processed meat in general containing myoglobin. Specific examples of the target to be treated include meat such as pork, beef, and chicken, processed meat thereof, fish meat such as tuna, bonito, and salmon, and processed fish meat thereof. A preferred target is meat showing a red color. Processed meat as a target to be treated is not particularly limited as long as it is a food produced from meat. Examples of the processed meat include raw ham, sausage, and loin roll. The form of the meat or processed meat to be treated is not particularly limited either, and may be selected from, for example, block meat or minced meat, according to the intended use.

According to one aspect of the present invention, the reducing agent of the present invention is used in combination with a substance which substitutes iron in the heme group of myoglobin with zinc (hereinafter referred to as "iron-zinc substituting substance"). When the reducing agent of the present invention is used in combination with a substance whose action is different from the reducing agent, the color tone is further improved owing to multiple effect. In particular, the combination results in the maintenance of good color tone and prevention of color fading. Examples of the iron-zinc substituting substance include ferrochelatase (more specifically, see Japanese Unexamined Patent Application Publication No. 2006-61016). Ferrochelatase is present in animal tissues (particularly viscera), plant tissues (for example, mushrooms, bean sprouts, and pea bean), yeasts (for example, bread yeast, beer yeast, sake yeast, wine yeast, and shochu yeast), and bacteria. Ferrochelatase extracted from these natural products may be used. In addition, ferrochelatase is rich in mitochondria fractions, so that the use of mitochondria fractions are particularly preferred. The iron-zinc substituting substance may be a *Saccharomyces* yeast (for example, beer yeast, bread yeast, sake yeast, or shochu yeast) (more specifically, see Japanese Unexamined Patent Application Publication No. 2005-87058).

This embodiment is characterized in that it uses the reducing agent of the present invention in combination with the iron-zinc substituting substance. Typically, the color tone improver of the present invention is provided as a combination agent composed of the reducing agent of the present invention and the iron-zinc substituting substance. On the other hand, for example, the color tone improver of the present invention may be provided in the form of a kit composed of the reducing agent of the present invention (first component) and an agent (second component) containing the iron-zinc substituting substance. In this case, the target to be treated (meat or processed meat) is treated simultaneously or consecutively by the first and second components. The term "simultaneously" does not mean strict simultaneousness. Accordingly, the concept "simultaneously" herein include the case wherein two components are used without time difference, such as the use of these components after mixing them, and the case wherein two components are used substantially without time difference, such as the use of one component immediately after the use of the other component.

When the reducing agent of the present invention is used as a color tone improver, the color tone improver may contain, in addition to the active ingredient (polypeptide) and additives (for example, an excipient, a buffering agent, a suspending agent, a stabilizer, a pH controlling agent, a preservative, an antiseptic, a perfume, a thickener, an oil or fat, a brightener, a binder, a binding reinforcer, an emulsification stabilizer, or a normal saline solution), a condiment, a spice, a masking agent, a softener, or the like. Examples of the condiment include soy sauce, miso, vinegar, sake, mirin (Japanese sweet rice wine for cooking), salt, soup stock of bonito or kelp, meat extract, or vegetable extract. Examples of the spice include pepper, laurel, thyme, clove, oregano, star anise, Japanese pepper, sage, parsley, nutmeg, mustard, ginger, cinnamon, basil, paprika, rosemary, spearmint, lemon glass, tarragon, chervil, cardamom, cumin, coriander, dill, fennel, marjoram, and allspice. Examples of the masking agent include saccharides such as sucrose and cyclodextrin; and herbs such as clove, allspice, laurel, cinnamon, and nutmeg. Examples of the softener include proteolytic enzymes such as protease, trypsin, chymotrypsin, papain, bromelain, and ficin.

The reducing agent of the present invention may be used for meat or other targets. The reducing agent of the present invention may be used for the purpose of reduction or oxidation prevention (including color fading prevention) of a composition containing a heme protein other than myoglobin (for example, hemoglobin).

The reducing agent of the present invention is expected to be used for the measurement of the hemoglobin concentration and the treatment of hemoglobinemia. More specifically, the reducing agent of the present invention is useful as an active ingredient of reagents and medicines. At present, the cyanmethemoglobin method is frequently used for measuring the hemoglobin concentration of blood. According to the method, methemoglobin is subjected to the action of a mixture of potassium ferricyanide and potassium cyanide to form cyan methemoglobin, and measured by colorimetric determination. The reducing agent of the present invention can be used in place of the method for measuring the blood methemoglobin level or total methemoglobin content.

Methemogulobinemia is caused by oxygen deficiency in the body due to excessive accumulation of methemoglobin for some reason. The most effective treatment for methemogulobinemia is believed to be the intravenous injection of methylene blue. However, when methemogulobinemia is complicated with cyanide poisoning, methylene blue cannot be used because it accelerates cyanide poisoning. Examples of other treatment include oral administration and intravenous injection of ascorbic acid (ascorbic acid may be administered in combination with riboflavin), but these methods are not so effective. The reducing agent of the present invention allows a new treatment strategy which replaces these conventional treatment methods. The treatment using the reducing agent of the present invention may be used for patients to whom methylene blue cannot be administered (for example, patients having cyanide poisoning). In addition, methylene blue is ineffective for those lack in glucose-6-phosphate dehydrogenase (G6PD). The patients with disorders in the pentose phosphate pathway such as G6PD deficiency will not respond to the approach, and must receive urgent exchange transfusion.

G6PD deficiency is one of most common disorders in the world. About 10% male of black male in the United States have the disorder. Many patients are inhabitants in Africa and the Mediterranean. Accordingly, a substantial proportion of subjects are at risk of developing (oxidative) drug-induced methemogulobinemia. The administration of methylene blue to these patients is ineffective (because G6PD deficiency in them will cause NADPH deficiency), and can be counterproductive. The reducing agent of the present invention is expected to be effective for these patients.

The reducing agent of the present invention can exhibit pharmacological action and physiological action such as the reduction of burden on the heart caused by the disorders of cardiac rate, blood pressure, and cardiac output, and acceleration of metabolism in tissues. The medicine containing the reducing agent of the present invention is expected to be used as a tolerance enhancer for enhancing the body tolerance under physiological conditions with high oxygen demand of tissues, such as the environments with hard work and exercise. In addition, the medicine of the present invention may be used for prevention or treatment of cardiac failure, cardiac myopathy, myocarditis, myocardial infarction, pericarditis, perimyocarditis, transient ischemia attack, coronary heart disease, congenital anomaly with right to left arteriovenous shunt (vitia), tetralogy/pentalogy of Fallot, Eisenmenger's syndrome, shock, peripheral ischemia, arterial occlusive disease (AOD), peripheral AOD (pAOD), carotid artery stenosis, renal artery stenosis, microcirculatory disorders in the brain (arteriocapillary sclerosis), bleeding in the brain, cerebral vein blood clots and intracranial venous sinus thrombosis, angiodysplasia, subarachnoid hemorrhage, vascular dementia, Biswanger's disease, subcortical arteriosclerotic encephalopathy, multiple cortical infarction accompanied by embolization, vasculitis, diabetic retinopathy, prognosis of anemia due to various causes (for example, aplastic anemia, myelodysplastic syndrome, polycythemia vera, anemia megaloblastic, hypoferric anemia, renal anemia, sphaerocytosis, and haemolytic anemia), thalassemia, hemoglobinopathy, glucose-6-phosphate dehydrogenase deficiency, transfusion onset, rhesus incompatibility, malaria, valvuloplasty, acute post hemorrhagic anemia, hypersplenism, lung fibrosis, emphysema, lung oedema: ARDS, IRDS, or recurrent lung emphysema, burn, angina pectoris, ischemic disease such as hibernation, blood circulation disorder, hypoxia, or hypoxemia, or prevention or treatment of diseases accompanied by or caused by any of these diseases or symptoms.

In order to prevent ischemic cell damage through the supply of oxygen to the ischemic tissues (and to protect tissues from reperfusion injury), the medicine of the present invention may be administered before, during, and/or after the occurrence of ischemic event. In combination with the administration of the medicine of the present invention, a vasoactive oxygen carrier (for example, oxygen carrier based on hemoglobin) may be administered. For example, in order to achieve intended treatment effect in mammal against acute ischemia and following reperfusion and release of free radical caused by surgical revascularization (for example, percutaneous transluminal coronary revascularization), transplantation, acute myocardial infarction, or angioplasty (for example, percutaneous transluminal coronary angioplasty), the combination of the medicine of the present invention, a vasoactive carrier (for example, oxygen carrier based on heme protein), and gaseous nitric oxide may be administered, or the combination of the medicine of the present invention and a vasoactive carrier may be administered after the administration of gaseous nitric oxide. The mammal treated by the method described herein may have ischemic heart disease, acute ischemic condition (for example, myocardial infarction, cerebral apoplexy, or renal ischemia), or angiospasm in the organ (for example, brain, heart, kidney, liver, or gastrointestinal tract) before treatment.

The medicine of the present invention may be used for treating hypoxemic tissues in vertebrate animals caused by various factors including the decrease in the red blood cell flow rate in a part of or throughout the circulating system, anemia, and cerebral apoplexy. In addition, the medicine of the present invention may be prophylactically used for the purpose of preventing oxygen deficiency in tissues of vertebrate animals. Furthermore, the medicine of the present invention may be used for the purpose of treating or preventing hypoxia caused by partial block in partial arterial obstruction or minute circulation. Regarding the administration of hemoglobin, see U.S. patent application Ser. No. 08/409,337.

The dose and administration period of the medicine of the present invention are not particularly limited, and may be appropriately selected in accordance with the administration form, age, body weight, symptoms, and the like.

The subject of the medicine of the present invention is not limited, and include humans, mammals other than humans (including pet animals, livestock, and experimental animals; specific examples include monkeys, mice, rats, guinea pigs, hamsters, monkeys, bovines, pigs, goats, sheep, horses, chickens, sheep, whales, dolphins, dogs, and cats). The treatment subject may have euvolemia, hypervolemia, or hypovolemia before, during, and/or after administration of the medicine of the present invention.

The administration form of the medicine of the present invention is not particularly limited. The medicine may be orally or parenterally administered. Examples of the "parenteral" administration used herein is not particularly limited, and examples thereof include intravenous, intramuscular, intraarterial, intraspinal, intracystic, intraorbital, intracardiac, intradermal, intraperitoneal, transtracheal, hypodermic, subepidermal, intracapsular, subcapsular, subarachnoid, intraspinal, and intrasternal infusion and injection. The administration form is preferably intravenous injection.

Examples of the preparation suitable for oral administration include tablets, capsules, powders, fine grains, granules, solutions, and syrups. Examples of the preparation suitable for parenteral administration include injections, suppositorys, inhalants, and patches. The medicine of the present invention may contain, as necessary, a pharmacologically and pharmaceutically acceptable additive. Examples of pharmacologically and pharmaceutically acceptable additive include excipients, disintegrating agents or disintegrating aids, binders, lubricants, coating agents, dyes, diluents, bases, solubilizers or solubilizing agents, isotonizing agents, pH adjusting agents, stabilizers, propellants, and adhesives.

The preparation suitable for oral administration or parenteral administration may contain additives such as excipients such as glucose, lactose, D-sorbitol, D-mannitol, starch, kaolin, xylitol, dextrin, corn starch, potato starch, hydroxypropyl cellulose, or crystalline cellulose; disintegrating agents or disintegrating aids such as carboxymethyl cellulose, starch, or carboxymethyl cellulose calcium; binders such as hydroxypropyl cellulose, hydroxypropyl methyl cellulose, polyvinyl pyrrolidone, or gelatin; lubricants such as light anhydrous silicic acid, synthetic aluminium silicate, stearic acid, calcium stearate, magnesium stearate, or talc; coating agents such as hydroxypropyl methyl cellulose, white sugar, polyethylene glycol, or titanium oxide; bases such as vaseline, liquid paraffin, polyethylene glycol, gelatin, kaolin, glycerin, purified water, or hard fat; propellants such as Freon, diethyl ether, or compressed gas; adhesives such as sodium polyacrylate, polyvinyl alcohol, methyl cellulose, polyisobutylene, or polybutene; additives for preparations such as base cloth including cotton cloth or plastic sheet. Examples of the preparation suitable for injection include solubilizers or solubilizing agents suitable as a component of an aqueous injection or an injection which is dissolved before use such as distilled water, normal saline solution, or propylene glycol; isotonizing agents such as glucose, sodium chloride, D-mannitol, and glycerin; pH controlling agents such as organic acids (for example, itaconic acid, succinic acid, tartaric acid, fumaric acid, citric acid, malic acid, adipic acid, gluconic acid, pyrophosphoric acid, lactic acid, α-ketoglutaric acid, or phytic acid) or salts of these organic acids, inorganic acids (for example, carbonic acid) or salts of these inorganic acids, acidic amino acids (for example, aspartic acid or glutamic acid), basic amino acids (for example, arginine, lysine, or histidine); and soothing agents such as lidocaine.

One of typical targets of the medicine of the present invention is hemoglobin. The hemoglobin is not particularly limited, and may be natural (unmodified) hemoglobin, genetically modified hemoglobin, or chemically modified hemoglobin treated by chemical reaction such as intramolecular or intermolecular crosslinking, polymerization, or addition of chemical group (for example, polyalkylene oxide, polyethylene glycol, superoxide dismutase, or other adduct). The medicine of the present invention may be used to a heme protein other than the hemoglobin, and also to a metalloporphyrin complex having a similar structure to the heme protein.

3. Method for Producing Reducing Agent

Another aspect of the present invention provides a method for producing the reducing agent of the present invention. The production method of the present invention includes a step of culturing a heme reductase, preferably a microorganism belonging to the genus Bacillus producing a metmyoglobin reductase under conditions suitable for the production of the enzyme (step (1)), and a step of recovering the enzyme from the culture (step (2)).

The microorganism belonging to the genus Bacillus in the step (1) is preferably a microorganism selected from the group consisting of Bacillus subtilis, Bacillus amyloliquefaciens, Bacillus natto, Bacillus thuringiensis, and Bacillus mycoides. The culture method and culture conditions are not particularly limited as long as the intended enzyme is produced. More specifically, the culture method and culture conditions suitable for the culture of the microorganism to be used are appropriately established with the proviso that a polypeptide exhibiting heme reduction activity is produced. As examples of the culture conditions, the culture medium, incubation temperature, and incubation time are described below.

The culture medium is selected from those that allows the growth of the microorganism to be used. The medium may include a carbon source such as arabinose, xylose, glucose, fructose, galactose, sucrose, gentiobiose, soluble starch, glycerin, dextrin, molasses, or an organic acid, a nitrogen source such as ammonium sulfate, ammonium carbonate, ammonium phosphate, ammonium acetate, corn gluten meal, soybean powder, casamino acid, ground coffee, cottonseed oil cake, peptone, yeast extract, corn steep liquor, casein hydrolysate, bran, or meat extract, and an inorganic salt such as a potassium salt, a magnesium salt, a sodium salt, a phosphate, a manganese salt, an iron salt, or a zinc salt. In order to accelerate the growth of the microorganism to be used, the culture medium may further contain, for example, a vitamin or an amino acid. The microorganism is cultured under aerobic conditions, wherein the pH of the culture medium is, for example, about 3 to 8, preferably about 5 to 7, the incubation temperature is normally about 10 to 50° C., preferably about 25 to 35° C., the incubation period is about 1 to 15 days, and preferably about 3 to 7 days. Examples of the culture method include stationary culture, shaking culture, and aerobic submerged culture using a jar fermenter.

After culturing under the above-described conditions, the intended enzyme is recovered from the culture (step (2)). Typically, after the operation of collecting the bacterial cells from the culture (step (2-1)), crushed bacterial cells are prepared (step (2-2)). The collection of the bacterial cells may be achieved by, for example, centrifugation or filtration. When a solid medium is used, the solid components other than the bacterial cells are preferably removed in advance. Preparation of the crushed bacterial cells may be achieved by mechanical crushing using a French press or Dyno-Mill, ultrasonication, or freezing crushing. When the bacterial cells can be crushed during the freezing treatment, drying treatment, or freeze-drying treatment, the step of crushing the bacterial cells may be unnecessary. The prepared crushed bacterial cells are used as the reducing agent of the present invention after additional treatment or untreated (more specifically, without special treatment). Examples of the "additional treatment" include concentrated (for example, concentration using an ultrafilter), purification (for example, salting-out or various chromatography), addition of other components, dilution, and drying. The additional treatment may include two or more kinds of treatment. The final state may be liquid or solid (including powder).

EXAMPLES

In order to find the substance which improves the color tone of meat, screening was carried out mainly on microorganism belonging to the genus *Bacillus*. The results of the experiments on the microorganism strains, which had been regarded as having high usefulness based on the result of screening, are described below.

1. Preparation of freeze-dried powder of *Bacillus subtilis*, *Bacillus amyloliquefaciens*, *Bacillus natto*, *Bacillus thuringiensis*, *Bacillus mycoides*

10 mL of the liquid medium shown in Table 1 was poured into a test tube, and sterilized at 120° C. for 20 minutes. As preculture, 1 Öse portion of *Bacillus subtilis* strain JCM1465 (=strain ATCC6051, IAM12118, and IFO13719), *Bacillus amyloliquefaciens* strain NBRC15535 (=strain ATCC23350), *Bacillus natto*, *Bacillus thuringiensis* strain NBRC13865 (=strain ATCC13366), and *Bacillus mycoides* strain IAM1190 (=strain IFO3039) each was inoculated in the test tube, and cultured overnight at 30° C. under shaking at 300 rpm.

TABLE 1

|  | %(w/v) |
| --- | --- |
| Glucose | 2 |
| Yeast extract | 1 |
| Peptone | 2 |

In the next place, 100 mL of the liquid medium shown in Table 1 was poured into a 300-mL conical flask, sterilized at 120° C. for 20 minutes, and used as the main culture medium. As the main culture, 1 mL of the preculture solution was inoculated, and cultured overnight at 30° C. under shaking at 200 rpm. The culture solution was centrifuged at 5,000 rpm for 5 minutes, and thus obtaining bacterial cells. The bacterial cells thus obtained were washed once with 30 mL of 20 mM phosphoric acid buffer (pH 7.5), and suspended in 30 mL of 20 mM phosphoric acid buffer (pH 7.5). The resultant suspension was frozen at −40° C. for 24 hours. Subsequently, freeze-drying (20° C., 24 hours) was carried out, and thus obtaining a freeze-dried powder (the bacterial cells were crushed by freeze-drying).

2. Meat Color Development Test 1

0.1 g of the freeze-dried powder was dissolved in 50 µL of 0.5 M phosphoric acid buffer (pH 5.5). Subsequently, 2 g of minced ham was mixed with the above-described powder solution and 50 µL of 4% (w/v) myoglobin, hermetically sealed, and allowed to stand at 4° C. for 17 hours. The change of the red color of the meat (degree of color development) was visually observed. As control test, a sample without the powder solution and another sample containing the powder solution boiled for 10 minutes were subjected to the same test. The results are shown in Table 2. The result of the treatment of *Pichia farinose* strain IAM12223 (=strain IFO0465, JCM1634) with a freeze-dried powder solution is also shown (data of untreated sample alone).

TABLE 2

| Sample | | Degree of color development |
| --- | --- | --- |
| *Bacillus subtilis* | Untreated | ++ |
| | Heat treated | − |
| *Bacillus amyloliquefaciens* | Untreated | + |
| | Heat treated | − |
| *Bacillus natto* | Untreated | ++ |
| | Heat treated | − |
| *Bacillus thuringiensis* | Untreated | + |
| | Heat treated | − |
| *Bacillus mycoides* | Untreated | + |
| | Heat treated | − |
| *Pichia farinose* | Untreated | − |
| | Heat treated | No data |
| None | | − |

++: developed strong color, +: developed color, −: developed no color

As described above, the freeze-dried powders of the test strains (*Bacillus subtilis*, *Bacillus amyloliquefaciens*, *Bacillus natto*, *Bacillus thuringiensis*, and *Bacillus mycoides*) showed meat color development effect. In particular, *Bacillus subtilis* and *Bacillus natto* showed high effect. In addition, the cultured bacterial cells were crushed by French press to obtain samples, and these samples showed similar meat color development effect (no data shown).

3. Meat Color Development Test 2

10 mg of the freeze-dried powder (crushed bacterial cells of *Bacillus subtilis*) was dissolved in 100 µL of 0.5 M phosphoric acid buffer (pH 5.5). The solution was mixed with 10 mg of freeze-dried minced ham powder, 30 µL of 4% (w/v) myoglobin, 30 µL of 0.2 M NADH, and 400 µL of sterilized water, and allowed to stand at room temperature for 30 minutes. Subsequently, the reaction liquid was centrifuged at 15,000 rpm for 15 minutes, and the supernatant was recovered. The absorption spectrum of the resultant supernatant at wavelengths from 700 nm to 400 nm was measured using a spectrophotometer. As control test, a sample containing the powder solution boiled for 10 minutes was subjected to the same test. The results are shown in FIG. 1. As is evident from the results, the untreated sample showed absorption maxima at 545 nm and 580 nm, indicating a red color.

4. Meat Color Development Test 3

Figure 2:
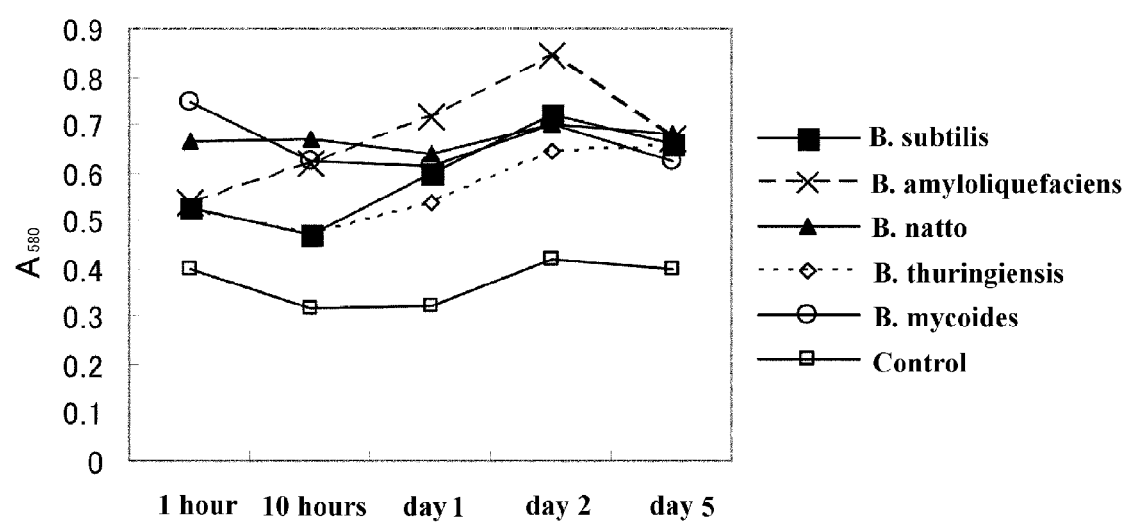
FIG. 2 shows the changes over time in the absorbance at 580 nm ($A_{580}$) of solutions each containing the crushed bacterial cell extract of a microorganism belonging to the genus *Bacillus* and freeze-dried ham powder.

According to the method described in 3, meat color development test was carried out using the freeze-dried powders prepared in 1. As control, a sample without the powder solution was subjected to the same test. The absorbance of the samples at a wavelength 580 nm is shown in FIG. 2. The result indicates that all the tested samples developed stronger color than the control even five days after.

5. Measurement Method for Metmyoglobin Reductase Activity

The metmyoglobin reductase activity was measured as follows. Firstly, the freeze-dried powders prepared in 1 were dissolved in water to make 10 mg/mL solutions, and used as the enzyme solutions. Subsequently, 100 µL of 0.1% (w/v) myoglobin and 150 µL of enzyme solution were added to 200 µL of 0.1 M phosphoric acid buffer (pH 5.5), and preincubated at 30° C. for 5 minutes. Thereafter, 50 µL of 1 mM NADH was added, and the change in the absorbance at a wavelength of 406 nm was measured for 5 minutes. The activity was expressed in unit (U). Under the present conditions, the amount of enzyme reducing substantially 1 µM of metmyoglobin in 1 minute was regarded as 1 U. For comparison, the enzymatic activity of the freeze-dried powder of *Pichia farinosa* strain IAM 12223 (=strain IFO0465, JCM1634) was also studied.

Figure 3:
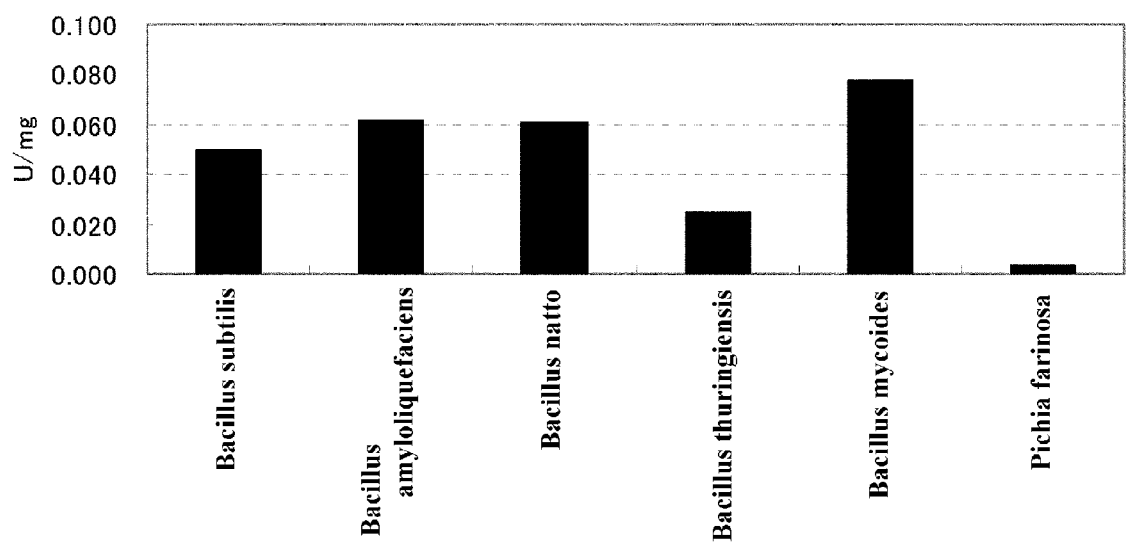
FIG. 3 shows the metmyoglobin reductase activity in the freeze-dried powder of the crushed bacterial cell extracts of microorganisms belonging to the genus *Bacillus*.

The measurement result is shown in FIG. 3. The freeze-dried powders with high meat color development effect exhibited high metmyoglobin reductase activity. The result indicates that the test strains (*Bacillus subtilis, Bacillus amyloliquefaciens, Bacillus natto, Bacillus thuringiensis*, and *Bacillus mycoides*) produce metmyoglobin reductase, and the color development effect is brought about by the enzymatic action.

6. Purification of Metmyoglobin Reductase

The metmyoglobin reductase was purified as follows. The bacterial cells of *Bacillus subtilis* obtained by culture described in 1 was crushed by French press, centrifuged, and then the supernatant was salted out with ammonium sulfate. The supernatant was treated at 30% saturation and collected, and treated at 70% saturation and centrifuged, and then the precipitate was recovered. The precipitate was dissolved in a 20 mM KPB (pH=6.0) solution, dialyzed, and used as the ammonium sulfate precipitation sample.

5 mL of the ammonium sulfate precipitation sample thus obtained was subjected to DEAE chromatography under the following conditions (DEAE column (HiTrap™ DEAE FF (5 mL); GE Healthcare)). As a result of this, the protein yield was 45.4%.

Figure 4:
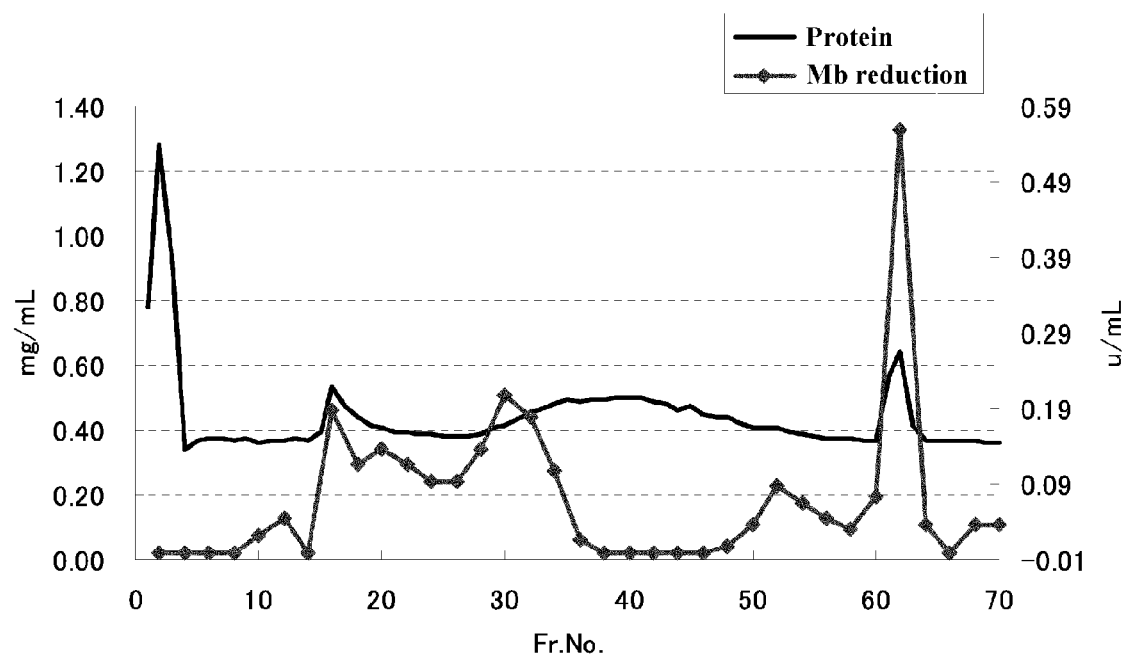
FIG. 4 shows the elution pattern and metmyoglobin reductase activity obtained by DEAE chromatography during purification of metmyoglobin reductase.

(DEAE Chromatography Conditions)
Carrier: DEAE HP (5 mL)
Charge: ammonium sulfate precipitation sample (5 mL)
Buf A: 20 mM KPB (pH 6)
Buf B: 20 mM KPB (pH 6), 1 M NaCl
Flow rate: 5 mL/minute
Fraction: 5 mL
Program: (1) Buf A washing 8 cv, (2) Buf B 10% washing 8 cv, (3) Buf B gradient 30%/25 cv, (4) Buf B 100% 8 cv FIG. 4 shows the elution pattern and metmyoglobin reductase activity obtained by the DEAE chromatography. The activity was measured by the decrease of A406, which is the absorption maximum of metmyoglobin. Of the fractions shown in FIG. 4, DEAE Fr. No. 61-63 with the highest activity were subjected to hydroxyapatite chromatography (hydroxyapatite column (1×5 cm) (TypeI 20 μm; Bio-Rad)) under the following conditions, thereby purifying the fractions. The protein yield of DEAE Fr. No. 61-63 was 98.5% as measured by hydroxyapatite chromatography.

Figure 5:
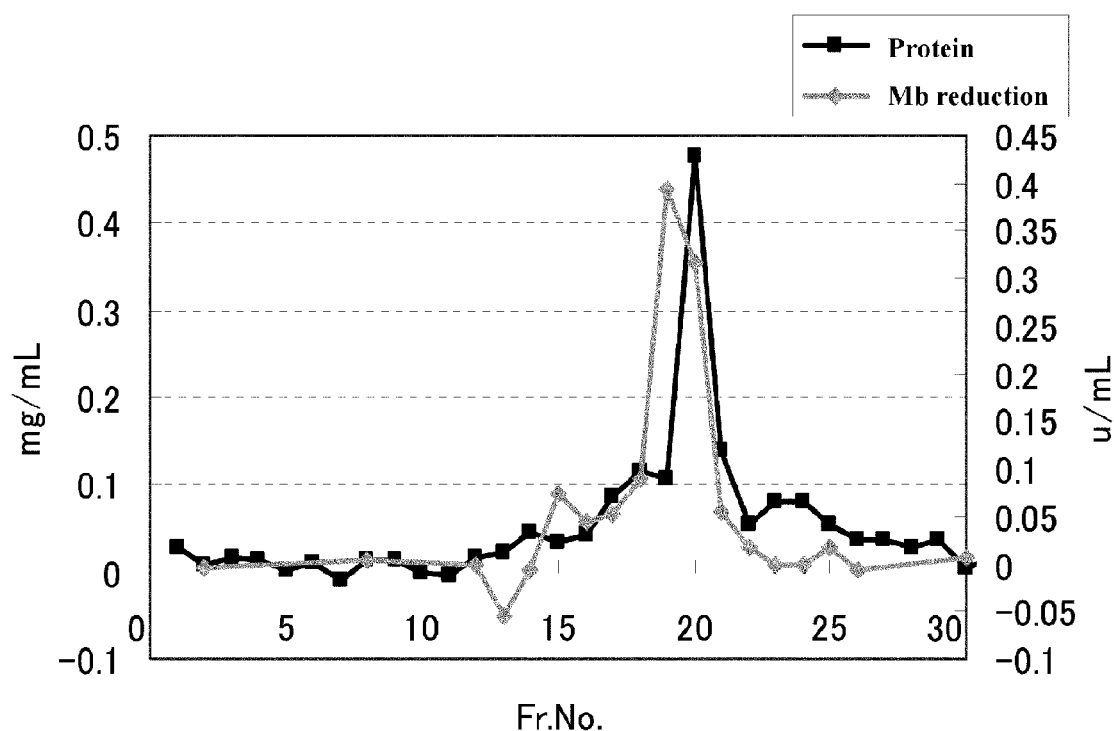
FIG. 5 shows the elution pattern and metmyoglobin reductase activity obtained by hydroxyapatite chromatography during purification of metmyoglobin reductase.

(Hydroxyapatite Chromatography Conditions)
Carrier: hydroxyapatite (5 mL)
Charge: DEAE purified Fr. No. 61-63
Buf A: 5 mM KPB, 0.3 M NaCl (pH 6)
Buf B: 400 mM KPB, 0.3 M NaCl (pH6)
Flow rate: 1 mL/minute
Fraction: 4 mL
Program: (1) Buf A washing 7 cv, (2) Buf B gradient 100%/20 cv, (3) Buf B 100% 10 cv FIG. 5 shows the elution pattern and metmyoglobin reductase activity obtained by hydroxyapatite chromatography of DEAE Fr. No. 61-63. The hydroxyapatite Fr. No. 19, which showed the highest specific activity in FIG. 5, was dialyzed with 20 mM KPB (pH 6), and then subjected to gel filtration chromatography under the following conditions (gel filtration column (Superdex TM75; GE Healthcare)).

Figure 6:
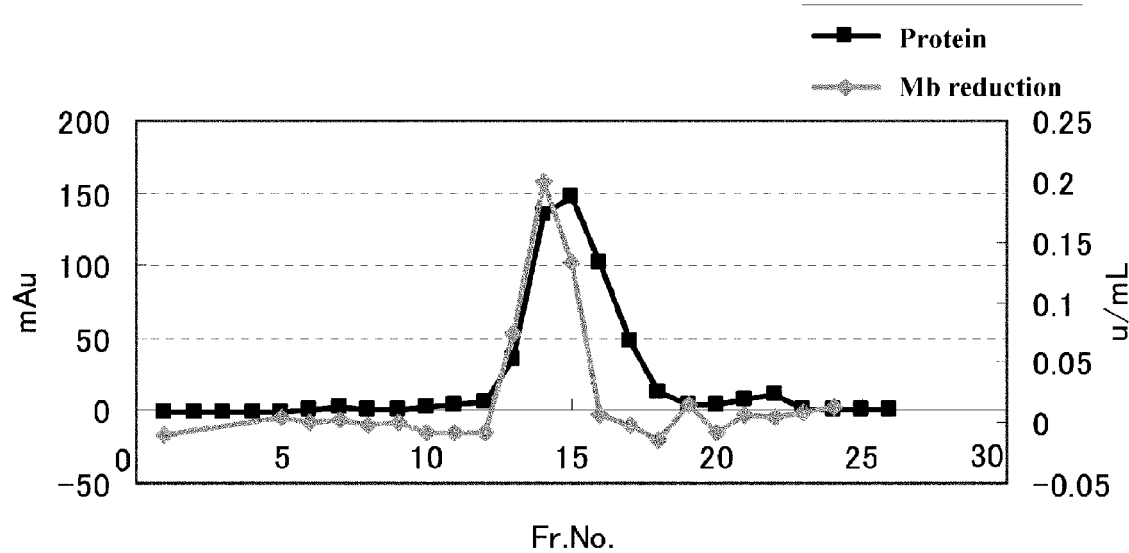
FIG. 6 shows the elution pattern and metmyoglobin reductase activity obtained by gel filtration chromatography after purification of metmyoglobin reductase.

(Gel Filtration Chromatography Conditions)
Carrier: Super dex 200 (120 mL)
Charge: Hydroxyapatite Fr.19
Buf A: 20 mM KPB (pH 6)
Flow rate: 1 mL/min
Fraction: 5 mL FIG. 6 shows the elution pattern and metmyoglobin reductase activity obtained by gel filtration chromatography of the hydroxyapatite Fr. No. 19. The gel filtration Fr. No. 12-16 containing the gel filtration Fr. No. 13-15, which showed particularly high specific activity in FIG. 6, was subjected to SDS-PAGE, and the band was confirmed (FIG. 7: gel filtration Fr. No. 12-16). The gel filtration Fr. No. 13-15 in FIG. 7 showed a single band.

FIG. 8 shows the specific activity of the fractions obtained in the above purification processes (DEAE chromatography, hydroxyapatite chromatography, and gel filtration chromatography). DEAE. Fr. No. 61-63 was subjected to gel filtration, and its specific activity was increased to about 20.7 times.

7. Amino Acid Sequencing of Metmyoglobin Reductase

Figure 7:
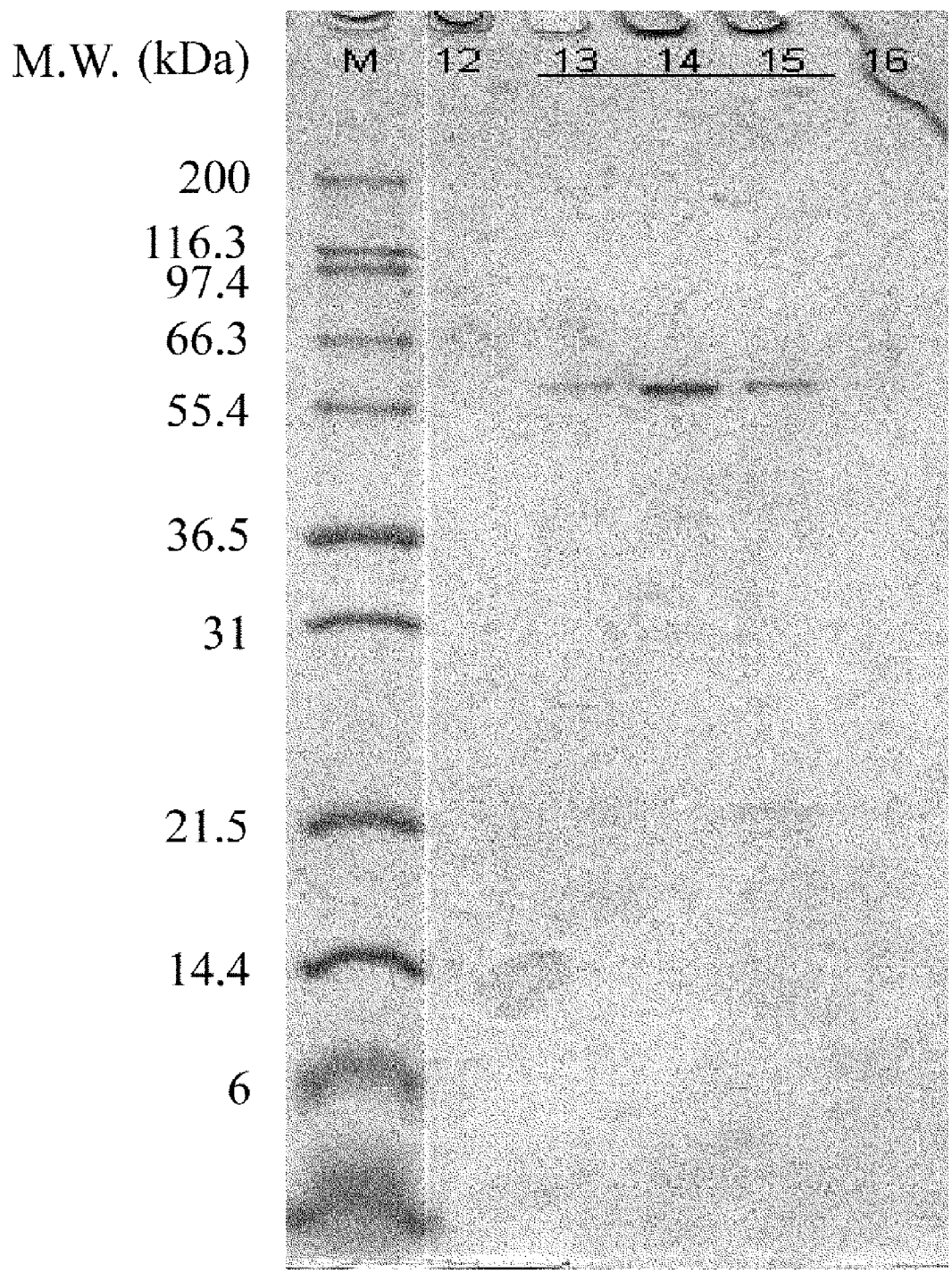
FIG. 7 shows the result of SDS-PAGE of the gel filtration fraction with high specific activity.

The single band obtained by SDS-PAGE shown in FIG. 7 was transferred to a PDVF membrane stained with Ponceau reagent, and cut out. The N-terminal amino acid sequence was analyzed by a protein sequencer. As a result of this, the N-terminal amino acid sequence was found to be VVGDFPI-ETDTLVIG (SEQ ID NO: 1). Furthermore, on the basis of the amino acid sequence, the gene was searched from the *Bacillus subtilis* database in BLAST. As a result of this, the gene was found to have 100% homology with pdhD (SEQ ID NO: 2) coding dihydrolipoyl dehydrogenase (hereinafter referred to as DLD). The amino acid sequence of DLD is shown in SEQ ID NO: 3.

8. Meat Color Development Test by DLD

Purified DLD was subjected to meat color development test. Using a freeze-dried powder sample of the purified DLD, meat samples were prepared as described below (Table 3), stored at 4° C. overnight, and compared (FIGS. 9 and 10).

TABLE 3

|  | Minced pork (g) | 40 mg/mL Mb(μL) | 0.5M KPB (μL) (pH = 5.5) | 20 mM NADH (μL) | Freeze-dried sample (mg) |
|---|---|---|---|---|---|
| Meat sample 1 | 2 | 37.5 | 37.5 | 37.5 | 0 |
| Meat sample 2 | 2 | 37.5 | 37.5 | 37.5 | 50 |
| Meat sample 3 | 2 | 37.5 | 37.5 | 37.5 | 20 |
| Meat sample 4 | 2 | 37.5 | 37.5 | 37.5 | 10 |
| Meat sample 5 | 2 | 37.5 | 37.5 | 0 | 50 |

Figure 9:
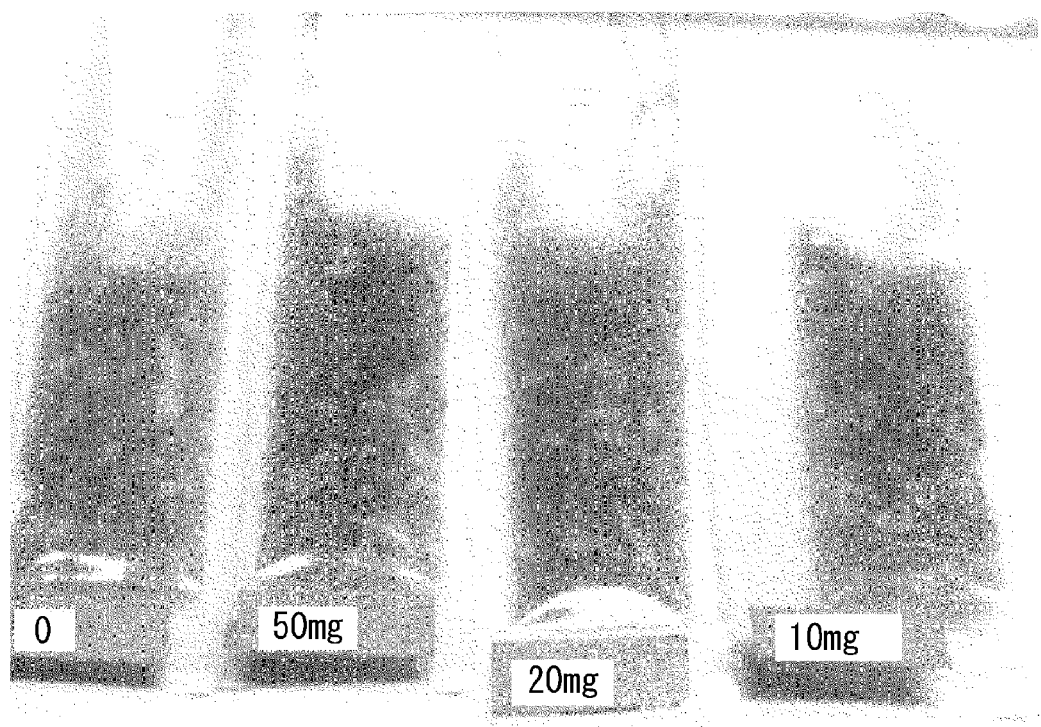
FIG. 9 shows the result of meat color development test using a purified enzyme (dihydrolipoyl dehydrogenase: DLD). The samples with different enzyme amounts were compared.
Figure 10:
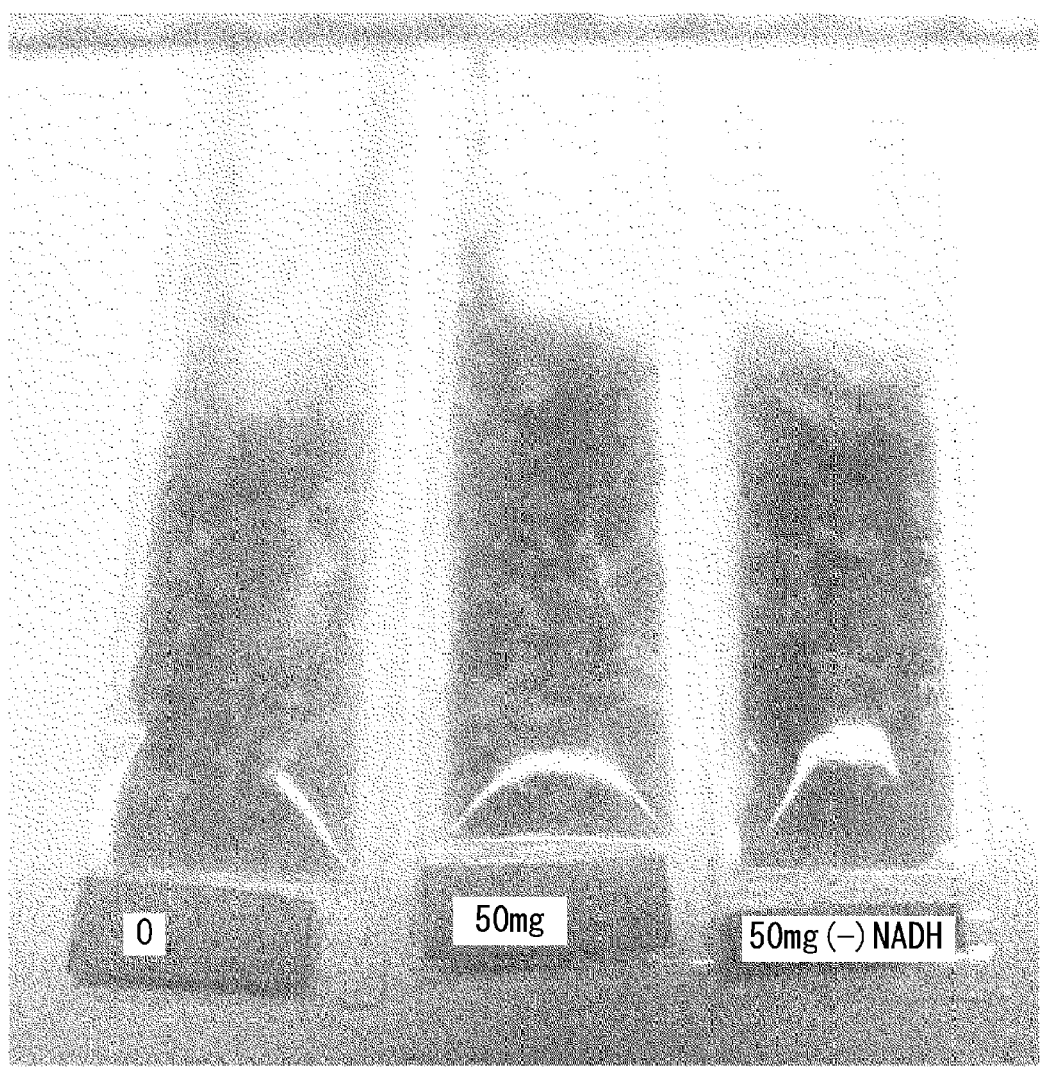
FIG. 10 shows the result of meat color development test using a purified enzyme (DLD). The samples with or without NADH were compared.

FIG. 9 shows meat samples with different enzyme contents (meat samples 1 to 4), indicating that DLD contributes to the improvement of color tone of meat. FIG. 10 shows the comparison of the color tone of meat with or without NADH (from left to right in this order, without freeze-dried powder (meat sample 1), with NADH (meat sample 2), and without NADH (meat sample 5)). It was confirmed that color development is sufficiently achieved even without NADH. The reason for this is likely that the meat contains a sufficient amount of NADH.

9. Enzymological Properties of DLD

Figure 11:
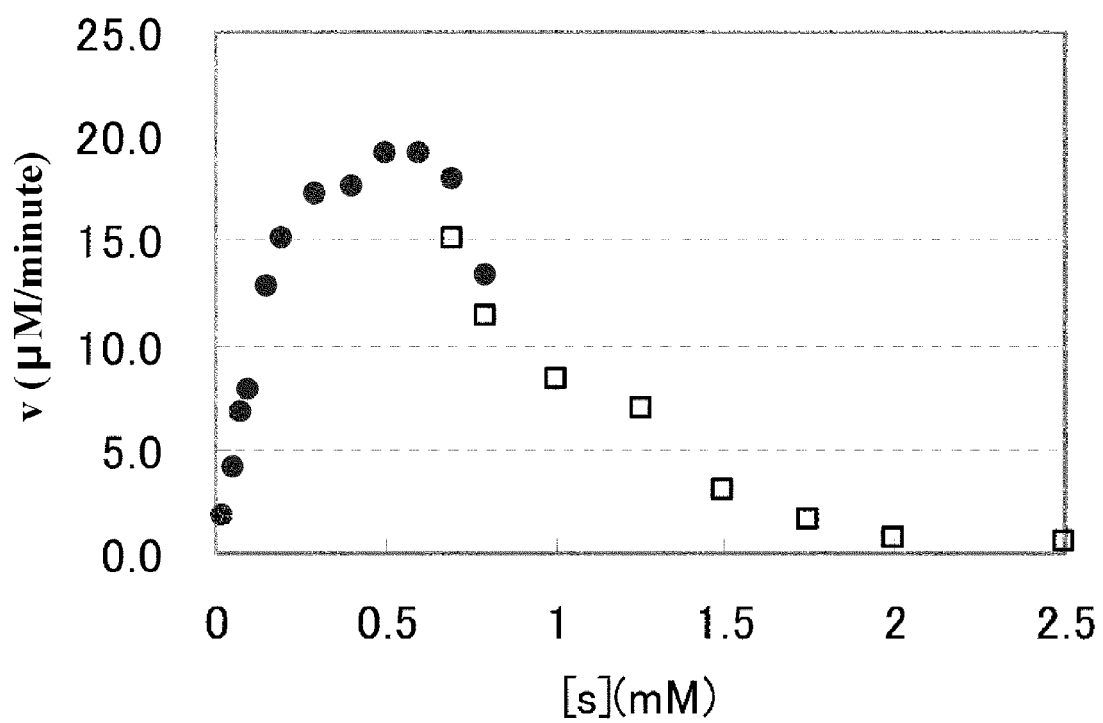
FIG. 11 shows the result of rate assay (substrate-saturation curve) of a purified enzyme (DLD).
Figure 12:
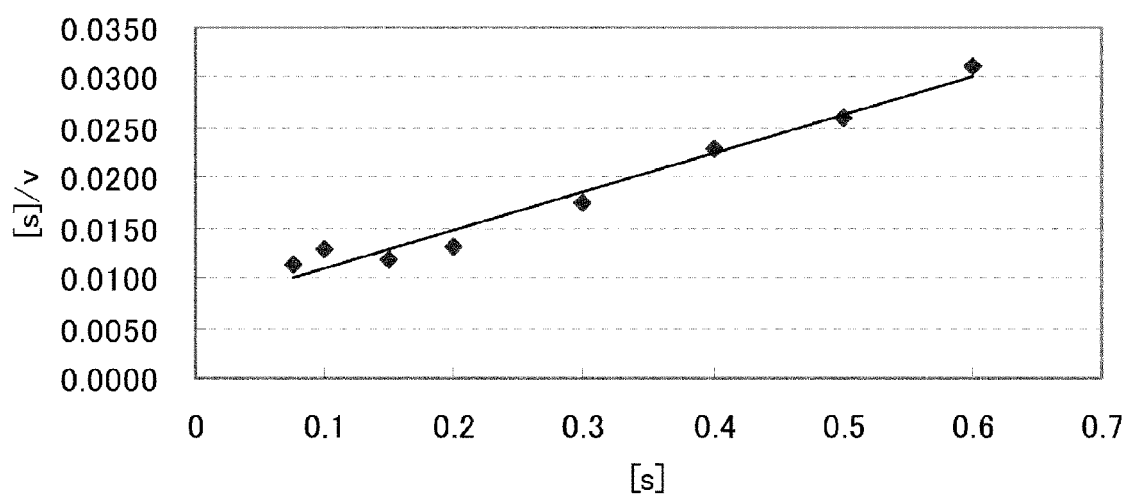
FIG. 12 shows the result of rate assay ([s]/v to [s] plot) of the purified enzyme (DLD).

Using potassium ferricyanide, which has high affinity for the enzyme, as the substrate, various properties were studied. Firstly, the substrate reactivity of DLD was examined. The amount of enzyme was 15 μL, and rate assay (pH=6.0) was carried out for 30 seconds to give the substrate concentrations (final concentrations) of 0.025, 0.05, 0.075, 0.1, 0.15, 0.2, 0.3, 0.4, 0.5, 0.6, 0.7, 0.8, 1.0, 1.25, 1.5, 1.75, 2.0, and 2.5 (mM). The molar absorptivity of potassium ferricyanide was 1.02× $10^3$ ($M^{-1} \cdot cm^{-1}$), and the rate (v) was expressed in the unit of μM/minute. The results are shown in FIGS. 11 and 12. The [s]/v to [s] plot was prepared from the rising of the substrate-saturation curve shown in FIG. 11 (FIG. 12), and the rate parameter (Kinetic parameter) was calculated (Km=0.19 (mM), Vmax=26.2 (μM/minute)). For comparison, the Km value of Diapholase from other source having high affinity for potassium ferricyanide is shown in Table 4. Table 4 indicates that the DLD obtained from *Bacillus subtilis* has higher affinity for potassium ferricyanide than the DLD derived from *C. kluyveri*.

TABLE 4

| Enzyme | Source | Km (mM) | Literature |
|---|---|---|---|
| lipoyl dehydrogenase | *C. kluyveri* | 0.35 | Frank Petrat. et. al(2003) The Journal of Biological Chemistry, 278, 46403-13 |
| NADPH-glutathione reductase | *C. kluyveri* | 0.13 | Frank Petrat. et. al(2003) The Journal of Biological Chemistry, 278, 46403-13 |
| NADH-cytochrome c reductase | *C. kluyveri* | 0.58 | Frank Petrat. et. al(2003) The Journal of Biological Chemistry, 278, 46403-13 |
| NADPH-cytochrome P450 reductase | *C. kluyveri* | 0.88 | Frank Petrat. et. al(2003) The Journal of Biological Chemistry, 278, 46403-13 |
| Diaphorase | *B. stearothermophilus* | 4.0 | Tomokazu Matsue et. al.(1990) Biochemica et Biophysica Acta, 1038, 29-38 |

Figure 13:
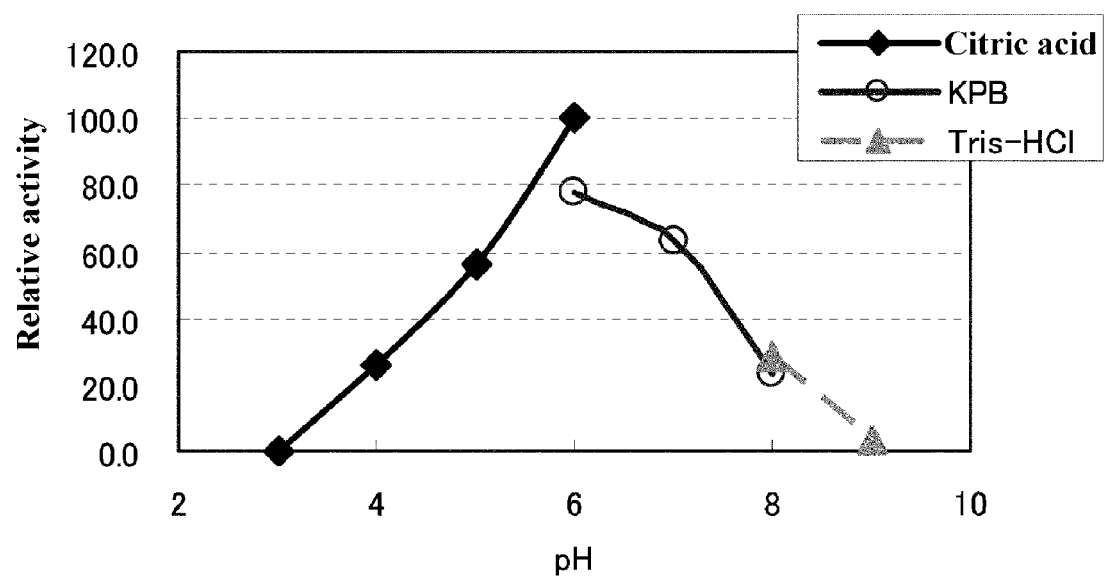
FIG. 13 shows the optimal pH of the purified enzyme (DLD).

The optimal pH of DLD was measured as follows. 50 μL of a 10-fold dilution (50 mM) of any of 0.5 M pH buffers (citric acid buffer (pH=3.0 to 6.0), potassium phosphate buffer (KPB) (pH=6.0 to 8.0), and Tris-hydrochloric acid buffer (pH=8.0 to 10.0)), 50 μL of 10-fold dilution (400 μM) of 4 mM potassium ferricyanide solution, 50 μL of enzyme sample, and 250 μL of MilliQ water were incubated at 30° C. for 5 minutes. Thereafter, 100 μL of 1 mM NADH solution was added, and the change in the absorbance at A420 was monitored. The result is shown in FIG. 13.

Figure 14:
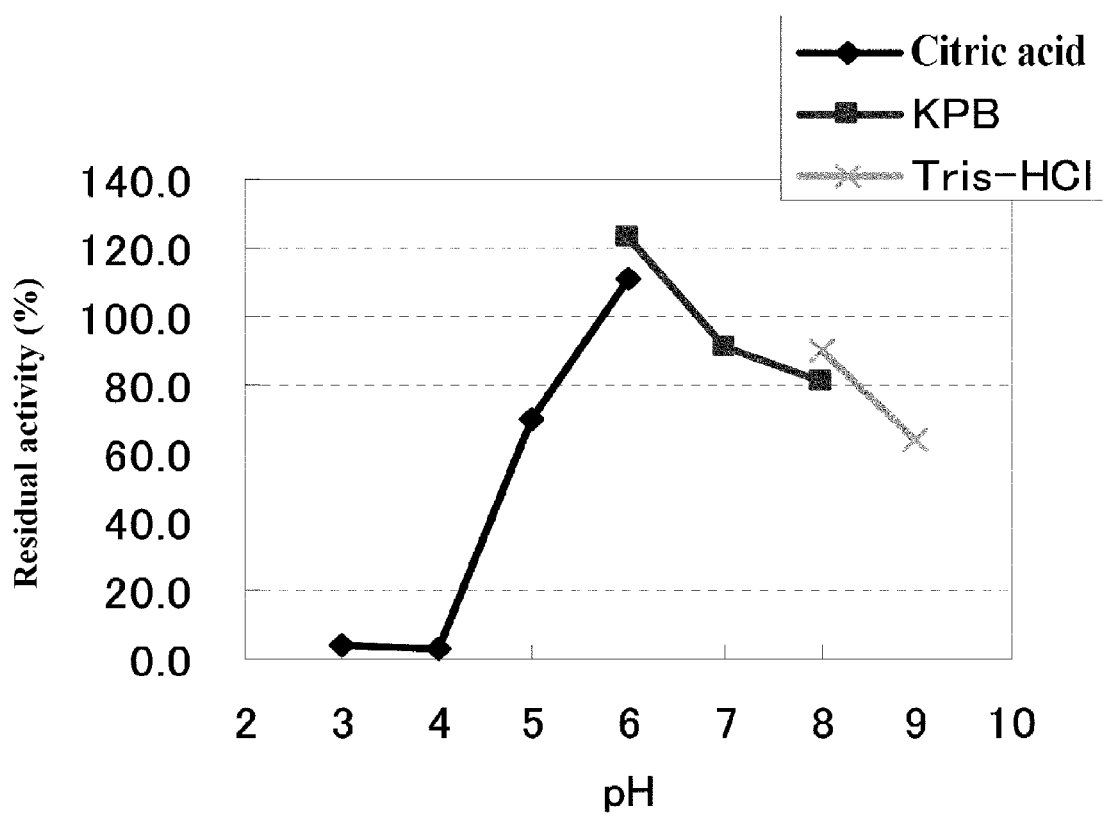
FIG. 14 shows the pH stability of the purified enzyme (DLD).

Subsequently, the pH stability of DLD was studied as follows. 20 μL of enzyme sample and 180 μL of any of 20 mM pH buffers (citric acid buffer (pH=3.0 to 6.0), potassium phosphate buffer (KPB) (pH=6.0 to 8.0), Tris-hydrochloric acid buffer (pH=8.0 to 10.0)) were mixed, the mixture was allowed to stand and react for 30 minutes, and used as the pH treatment sample solution. 150 μL of the pH treatment sample solution thus obtained, 100 μL of 0.5 M citric acid buffer (pH=6.0), and 100 μL of MilliQ water were mixed, and stored on ice overnight. To 350 μL of the resultant storage solution, 50 μL of 4 mM potassium ferricyanide was added, and incubated at 30° C. for 5 minutes. Thereafter, 100 μL of 1 mM NADH solution was added, the change in the absorbance at A420 was monitored for 30 seconds at intervals of 1 second (The activity of the sample without pH treatment was taken as 100%). The result is shown in FIG. 14. The stability in the lower pH side was insufficient, but the pH in meat was from 5 to 6, so that the activity is likely sufficient in meat.

The optimal temperature of DLD was measured as follows. 50 μL of 0.5 M citric acid buffer (pH 6), 50 μL of 2 mM potassium ferricyanide, 100 μL of MilliQ water, and 100 μL of 1 mM NADH were mixed, the mixture was preincubated at different temperatures for 5 minutes, and mixed with 200 μL of an enzyme sample. The change in the absorbance at A420 was measured for 5 minutes, thereby confirming the reaction.

Figure 15:
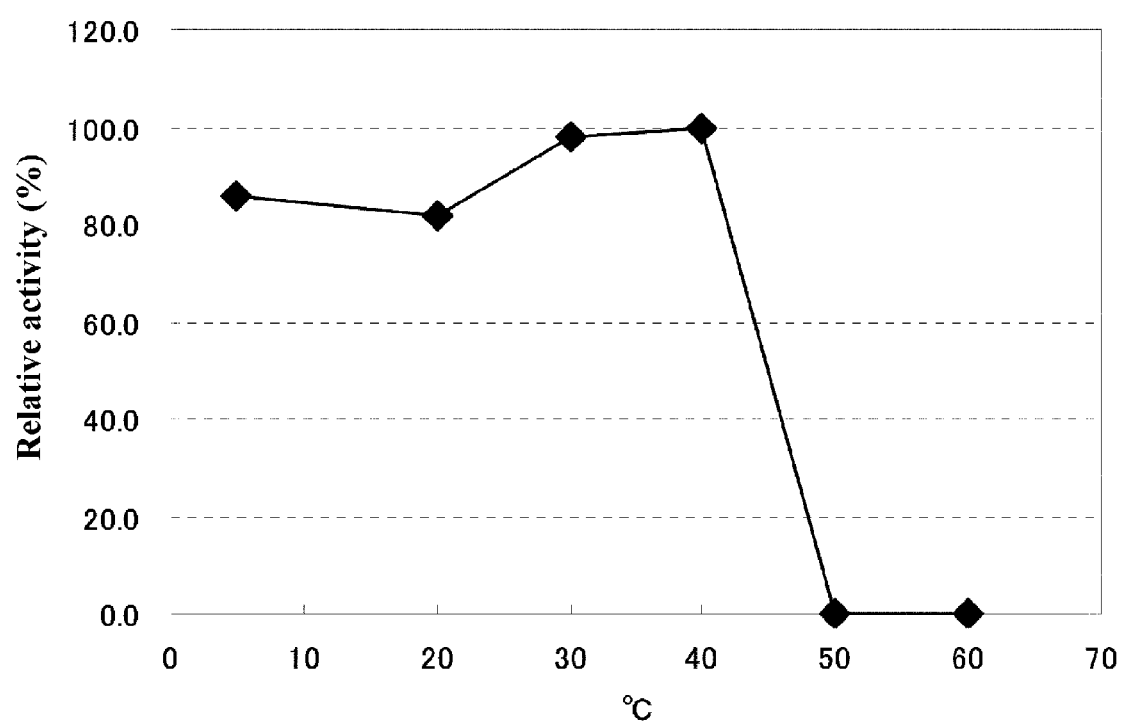
FIG. 15 shows the optimal temperature of the purified enzyme (DLD).

The result is shown in FIG. 15. The result indicates that the optimal temperature is 40° C., and deactivation occurs at 50° C.

Figure 16:
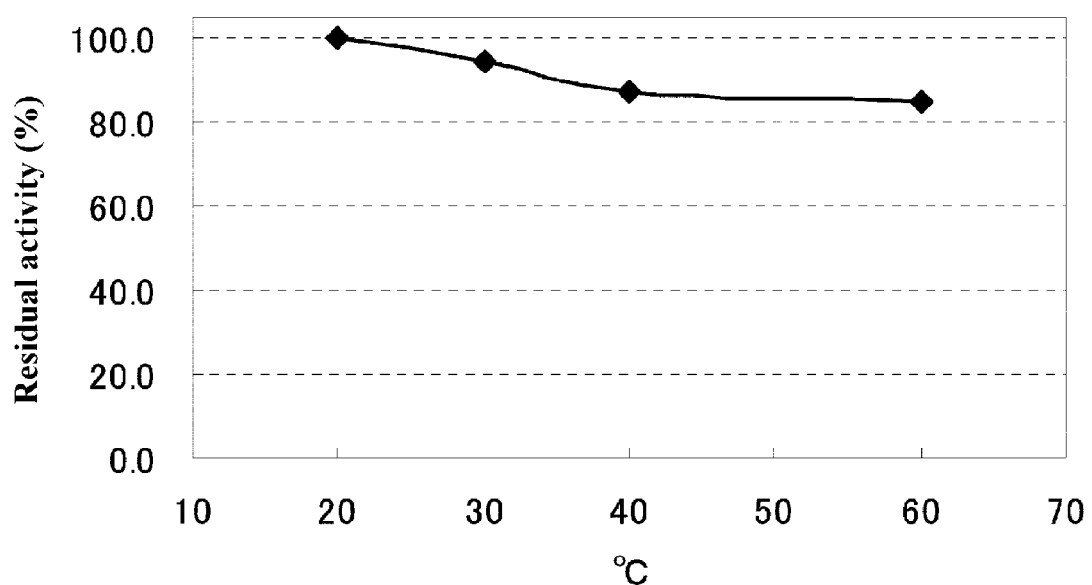
FIG. 16 shows the thermal stability of the purified enzyme (DLD).

Further, the thermal stability was measured as follows. The enzyme sample, which had been treated in advance for 30 minutes at different temperatures (30° C., 40° C., and 60° C.), was cooled on ice, and thus preparing treatment samples. 30 μL of the treatment sample was mixed with 50 μL of 0.5 M citric acid buffer (pH 6.0), 50 μL of 2 mM potassium ferricyanide, and 270 μL of MilliQ water, incubated at 30° C. for 5 minutes, and then mixed with 100 μL of 1 mM NADH solution. The change in the absorbance at A420 was measured for 30 seconds at intervals of 1 second. The result shown in FIG. 16 indicates that high activity remained even at 60° C.

Figure 17:
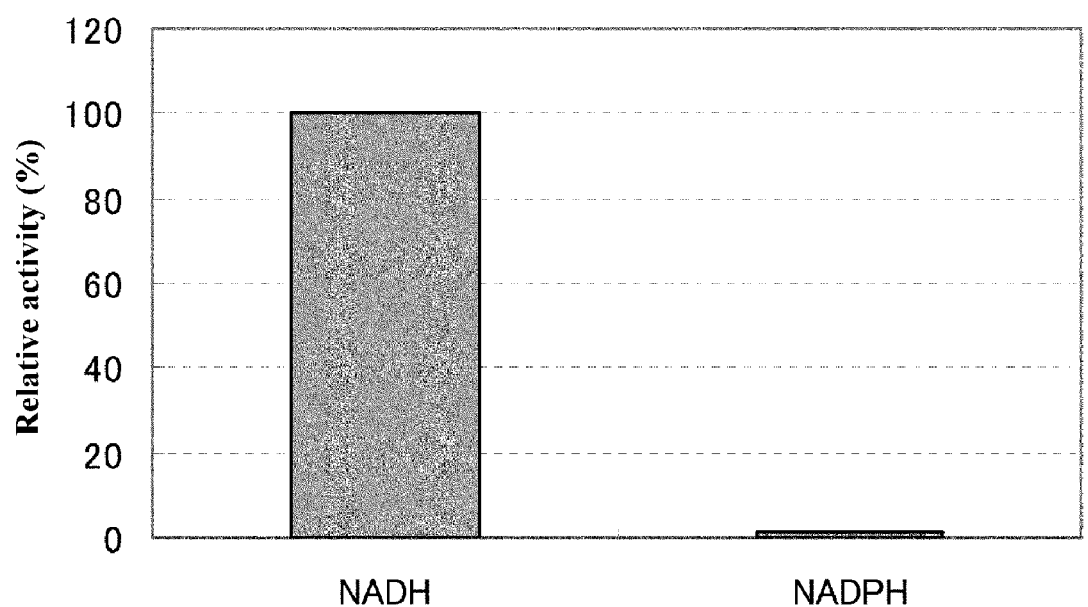
FIG. 17 shows the reactivity of the purified enzyme (DLD) to NADH and NADPH.

Subsequently, reactivity for NADH and NADPH was compared. 50 μL of 0.5 M KPB (pH 5.5), 100 μL of purified DLD, and 100 μL of 0.1% Mb were mixed, the volume was adjusted to 400 μL with MilliQ water, and preincubated at 30° C. for 5 minutes. Thereafter, 50 μL of 1 mM NaDH or NADPH was added, and A406 was monitored for 5 minutes. FIG. 17 shows the reactivity, taking the relative activity of NADH as 100(%). The result indicates that DLD has low reactivity for NADPH.

Figure 18:
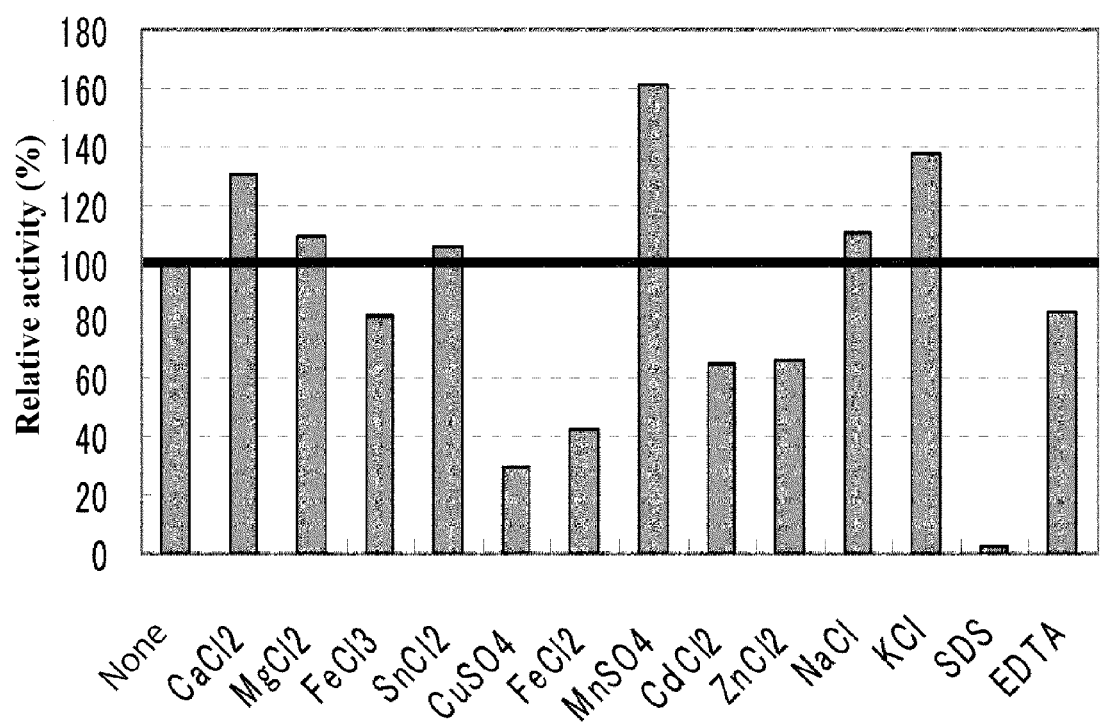
FIG. 18 shows the influences of various cations on the activity of the purified enzyme (DLD).

In addition, the influence of metal salts (metal cations) on the activity of DLD was studied. 100 μL of 500 mM KPB (pH 5.5), 200 μL of 0.1% (=13.4 μM) Mb, 150 μL of purified DLD, 10 μL of 100 mM cation ($CaCl_2$, $MgCl_2$, $FeCl_3$, $SnCl_2$, $CuSO_4$, $FeCl_2$, $MnSO_4$, $CdCl_2$, $ZnCl_2$, NaCl, KCl, SDS, or EDTA), and 100 μL of 1 mM NADH were mixed, and purified water was added to the mixture to make the volume 1 mL. The solution was used as the sample, and measured for the relative activity. The improvement in the activity was observed when $Ca^+$, $Mg^{2+}$, and $K^+$ were used (FIG. 18).

10. DLD Overexpression System

The DLD gene was obtained from *Bacillus subtilis*, and studied for establishing an overexpression system using *Escherichia coli*.

10-1. Genome Extraction from *Bacillus subtilis* Strain 7417

The genome extraction from *Bacillus subtilis* strain 7417 was carried out as follows. *Bacillus subtilis* strain 7417 was inoculated in a liquid medium (pH6.5) containing 0.5% peptone, 1.0% yeast extract, and 1.0% glucose, and cultured overnight at 30° C. under shaking at 300 rpm. The genome DNA was extracted from the culture thus obtained using QIA Quick™ Gel Extraction Test Kit (QIAGEN).

10-2. Amplification of DLD Gene by PCR DLD gene amplification by PCR was carried out as follows. 5 μL of 10× buffer, 4 μL of dTNP, 1 μL of the genome of *Bacillus subtilis*, 5 μL each of the following 10 μM primers (two types), and 0.1 μL of EX. Taq (DNA polymerase, Takara Bio Inc.) were mixed, and purified water was added to the mixture to make the volume 50 μL. The primers were combined in two patterns (patterns 1 and 2). The PCR reaction was carried out in two steps. Firstly, as the step 1, the solution was denatured by heat at 98° C. for 30 seconds. Subsequently, as the step 2, the following cycle (heat denaturation: 98° C., 10 seconds, annealing: 46° C., 30 seconds, elongation reaction: 72° C., 90 seconds) was repeated 25 times, and thus obtaining a PCR product.

(Primer Arrangement)

```
Pattern 1
DLD-Nde1-FW:
                                        (SEQ ID NO: 4)
GGCGTAATCATATGGTAGTAGGAG
```

-continued

DLD-BamH1-RV:
(SEQ ID NO: 5)
GATAGGATCCTTATTTTACGATG

Pattern 2
DLD-Nde1-FW:
(SEQ ID NO: 6)
GGCGTAATCATATGGTAGTAGGAG

DLD-BamH1-Histag-RV:
(SEQ ID NO: 7)
GATAGGATCCTTAGTGGTGGTGGTGGTGGTGTTTTA

CGATG 10-3. TA Cloning of DLD Gene

Subsequently, TA cloning of the DLD gene was carried out as follows. 3 μL of the PCR product obtained by PCR was mixed with 5 μL of 2× Liation buffer, 1 μL of pGEM-T easy vector, and 1 μL of T4 ligase. The mixture was allowed to react overnight at 4° C., thoroughly poured into competent cell DH5α, subjected to heat shock at 42° C. for 30 seconds, and cooled on ice for 2 minutes. 150 μL of SOC culture medium was added to this, and incubated at 37° C. for 20 minutes. The total amount was cultured on an LB/Amp culture plate, and thus obtaining colonies.

10-4. DLD Transformation

Subsequently, DLD was cloned into vector as follows. From the culture obtained by TA cloning, plasmid was extracted using GenElute™ plasmid Miniprep Kit (SIGMA). The plasmid extract thus obtained was mixed with 10× buffer, Nde I, and treated at 37° C. for 2 hours. Furthermore, 1 μL of BamH I was added, and treated at 37° C. for 1 hour to prepare a gene to be inserted. On the other hand, the pET20b vector was mixed with 1 μL of BamH I, and treated at 37° C. for 1 hour. In order to study the enzymatic activity of DLD with or without His-tag, samples were prepared as follows (unit is μL), and incubated at 16° C. for 30 minutes. Thereafter, the whole amount was added to competent cell DH5α, dissolved on ice for 1 hour, and the cell was subjected to heat shock (42° C., 30 seconds). The SOC culture medium was added to the cell, incubated at 37° C. for 20 minutes, and plated on an LB/amp culture medium.

10-5. Enzymatic Activity Measurement of Transformant

The activity of the transformant obtained as described above was measured as follows. Five colonies of DLD(+) Histag/pET20b/BL21 and four colonies of DLD(−) Histag/pET20b/BL21 were transferred to LB/Amp culture media, and cultured at 30° C. overnight under shaking (preculture). 60 μL of the preculture solution was inoculated in 3 mL of LB/Amp culture medium, and cultured at 37° C. overnight under shaking (main culture). When the OD600 reached 0.4 to 0.5, IPTG was added to give the final concentration of 0.1 mM, and cultured at 30° C. for 4 hours under shaking. The bacterial cells thus obtained were collected, and suspended in 50 mM Tris-HCl (pH=7.0). The suspension was crushed using a bead shocker (MULTI-BEADS SHOCKER, Yasui Kikai Corporation), centrifuged, and then the supernatant was used as the sample.

Enzyme reaction (metmyoglobin reduction reaction) was carried out as follows. 50 μL of the enzyme sample obtained by the above-described method was mixed with 0.5 M KPB buffer (pH=5.5) and 50 μL of 0.1% metmyoglobin solution, and purified water was added to the mixture to make the volume 225 μL. Subsequently, 25 μL of 1 mM NADH solution was added to initiate reaction, and the change in the absorbance at A406 was monitored for 10 minutes. At the same time, the protein amount was determined by Bradford assay. The results are shown in FIGS. 19 and 20.

Figure 19:
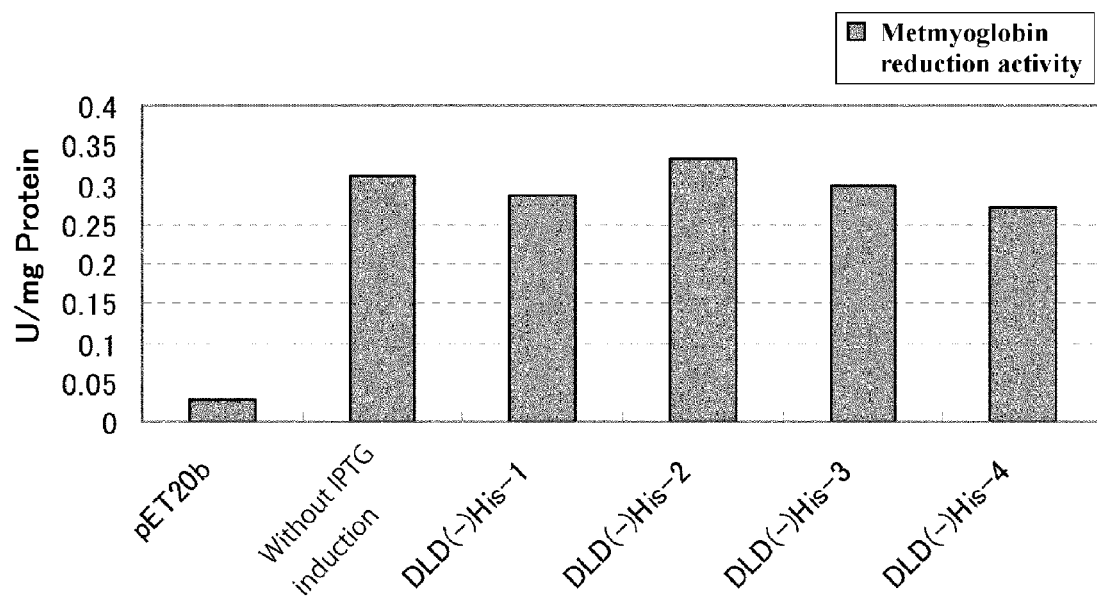
FIG. 19 shows the metmyoglobin reduction activity of recombinant DLD (without His tag).
Figure 20:
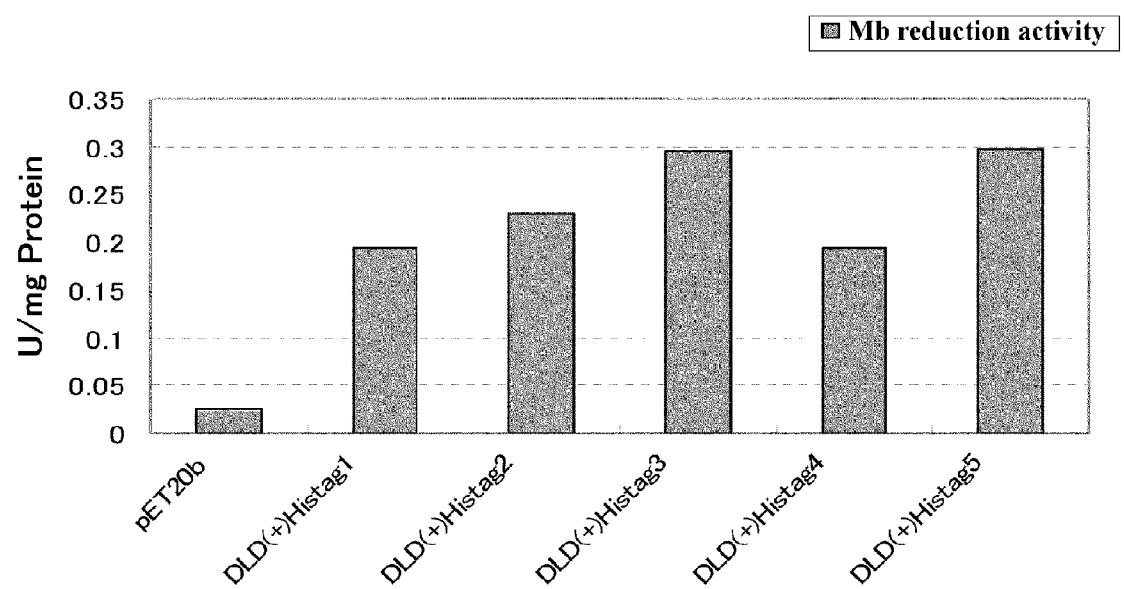
FIG. 20 shows the metmyoglobin reduction activity of recombinant DLD (with His tag).

FIGS. 19 and 20 show the metmyoglobin reduction activity of transformants without and with His-tag, respectively. For comparison, the data for the pET20b empty vector and IPTG vector are also shown. Both of them showed 10 times or more higher metmyoglobin reduction activity than the empty vector. As shown by the comparison of FIGS. 19 and 20, control by IPTG is likely not imposed.

11. Meat Color Development Activity of Recombinant DLD

The recombinant DLD obtained above was subjected to bead crushing, purified by an Ni-Sepharose column under the following conditions, and dianalyzed by 20 mM KPB (pH 6). After freeze-dried, it was used as the sample of meat color development test 1 and meat color development test 2.

(Chromatography Conditions)

Carrier: Ni Sepharose (25 mL)

Sample: crushed supernatant about 20 mL

Bind Buf: 20 mM KPB, 0.3 M NaCl (pH 6)

Elute Buf: 20 mM KPB, 0.3M NaCl, 0.4 M imidazole (pH 6)

Flow rate: charge: 5 mL/minute, other: 10 mL/minute

Fraction: 10 mL

Figure 21:
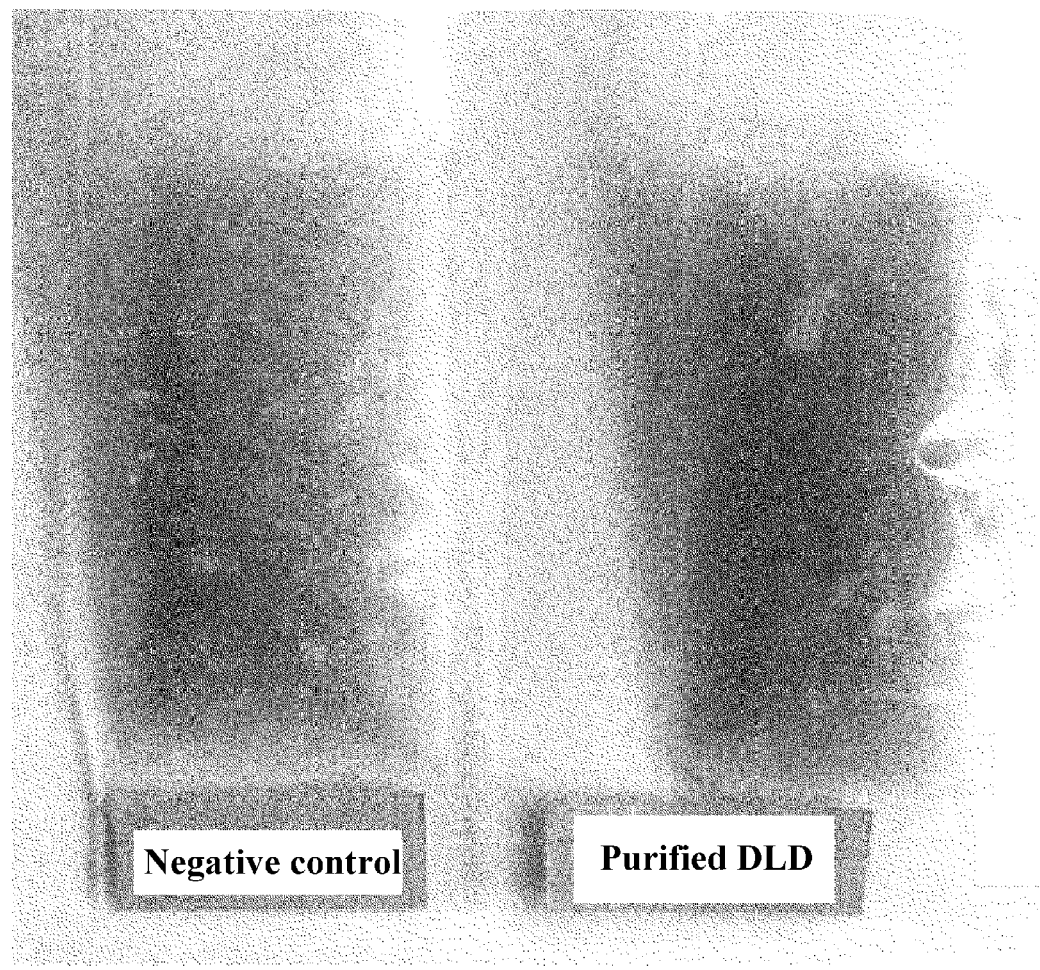
FIG. 21 shows the result of meat color development test using recombinant DLD. The R value, G value, and B value of the negative control (left) were 178, 104, and 102, respectively, and those of the purified recombinant DLD (right) were 210, 104, and 114, respectively.

Program: (1) Bind Buf washing 6 cv, (2) Elute Buf 10% washing 10 cv, (3) Elute Buf 100%/20 cv gradient, (4) Elute Buf washing 10 cv In meat color development test 1, 2 g of minced pork was mixed with 37.5 μL of 40 mg/mL (4%) myoglobin (SIGMA), 37.5 μL of 0.5 M KPB (pH=5.5), 37.5 μL of 20 mM NADH, and 66 mg of freez-dried enzyme powder sample was added, and allowed to react at 4° C. overnight. For comparison, a sample without freeze-dried powder (negative control) were also prepared. The results are shown in FIG. 21. The left shows the negative control, and the right shows the meat with the freez-dried powder. The change in the color tone was studied by visual observation and the RGB value of the image, and the results indicate that the color tone of the meat was more reddened by the recombinant DLD.

Figure 22:
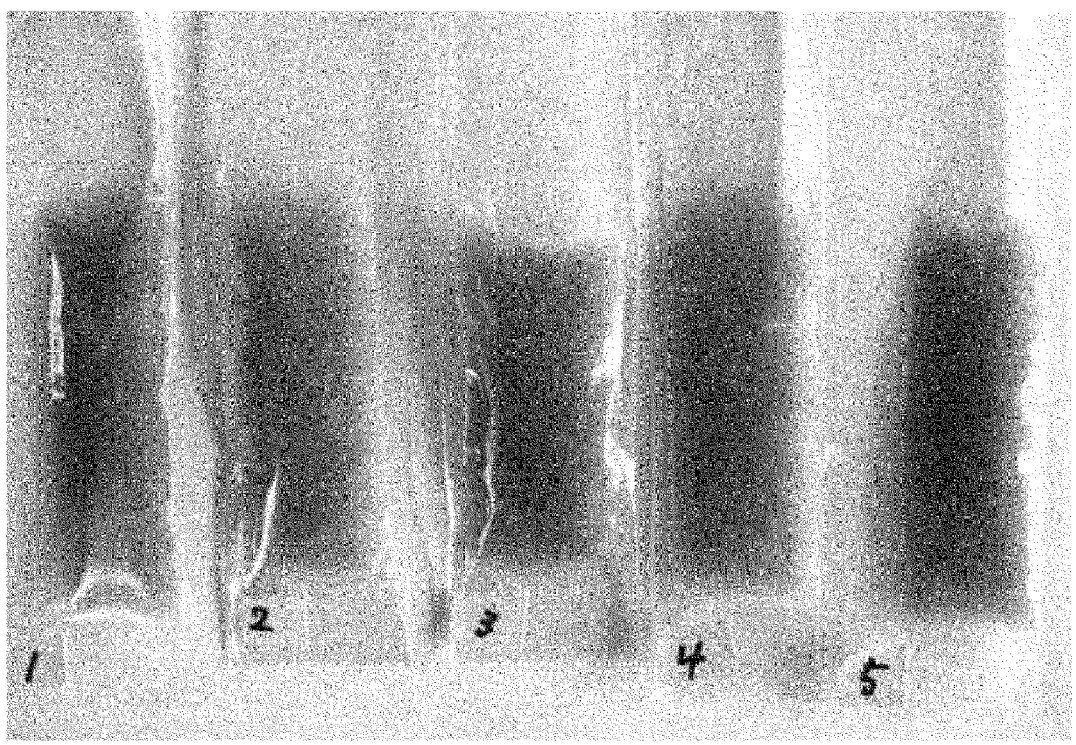
FIG. 22 shows the result of meat color development test using recombinant DLD. The R value, G value, and B value of sample 1 were 201, 117, and 123, respectively, those of sample 2 were 185, 121, and 105, those of sample 3 were 217, 97, and 93, those of sample 4 were 160, 108, and 83, and those of sample 5 were 156, 84, and 65, respectively.
Figure 23:
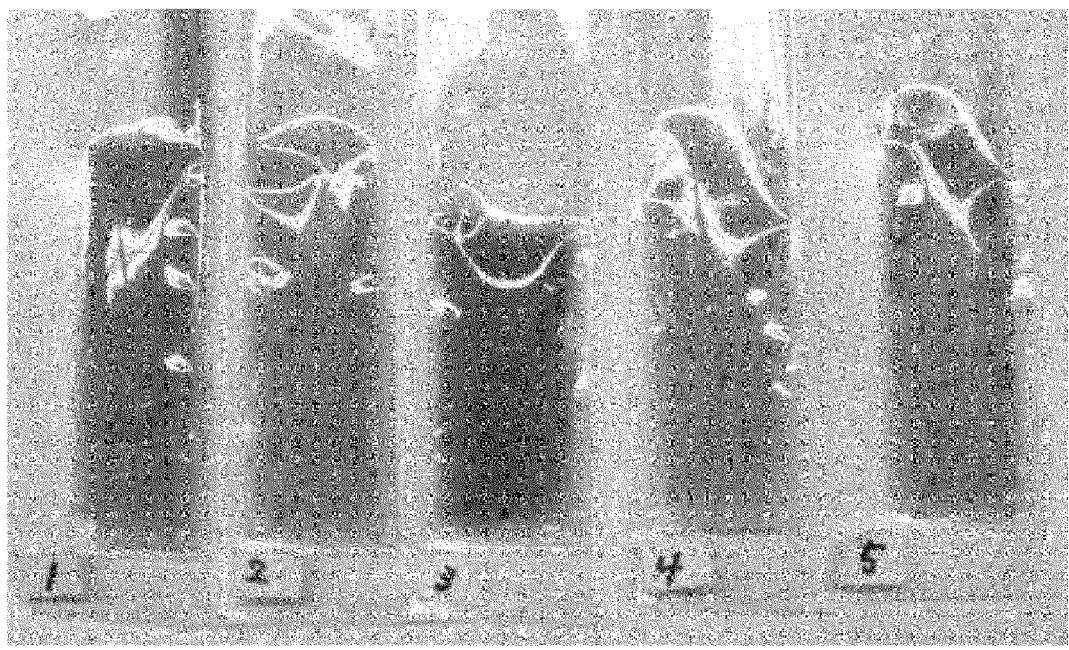
FIG. 23 shows the result of meat color development test using recombinant DLD. The R value, G value, and B value of sample 1 were 168, 122, and 106, respectively, those of sample 2 were 185, 152, and 145, those of sample 3 were 172, 123, and 119, those of sample 4 were 187, 153, and 144, and those of sample 5 were 173, 148, and 123, respectively.

In the meat color development test 2, 2 g of minced pork was mixed with 37.5 μL of 0.5 M KPB (pH=5.5), 37.5 μL of 40 mg/mL (4%) myoglobin (SIGMA), 37.5 μL of 20 mM NADH, and a sample ((1) purified DLD alone (60 mg), (2) food additive sodium nitrite alone (0.4% (w/w)=8 mg), (3) purified DLD+sodium nitrite ((1) and (2)), (4) mixture of (2) and zinc gluconate (15 mg), (5) none) and allowed to react at 4° C. overnight (FIG. 22). Furthermore, the reaction product was heated at 65° C. for 85 minutes, and the result is shown in FIG. 23. These samples shown in FIGS. 22 and 23 were studied by visual observation, and also by the RGB value of the images.

The color tone of the meat without heat treatment shown in FIG. 21 is described below. Good red color tone was found in the meat containing DLD (samples (1) and (3)). In particular, the color tone of the sample (3) containing DLD and sodium nitrite was good. The sample (4) containing sodium nitrite and zinc gluconate developed a brown color. The sample (2) containing sodium nitrite alone showed the similar color tone to the sample (5) without additive.

The color tone of the meat after heat treatment shown in FIG. 22 is described below. Good red color tone (white peach color) was found in the meat containing sodium nitrite (samples (2), (3), and (4)). In particular, the sample (3) containing DLD and sodium nitrite developed a strong red and showed a good color tone. The sample (1) containing DLD alone had rather stronger redness than the sample (5) without additive, but was markedly browned in comparison with the samples (2) to (4).

12. Purification of Meat Color Developing Enzyme

Of the meat color developing enzymes derived from the bacterial cells of Bacillus subtilis, the meat color developing enzymes other than DLD were purified. In the purification process, using the first half peaks of DEAE chromatography (DEAE. Fr. No. 27-35 shown in FIG. 4) as starting materials, phenyl chromatography, hydroxyapatite chromatography, and Cu affinity chromatography were carried out.

Figure 24:
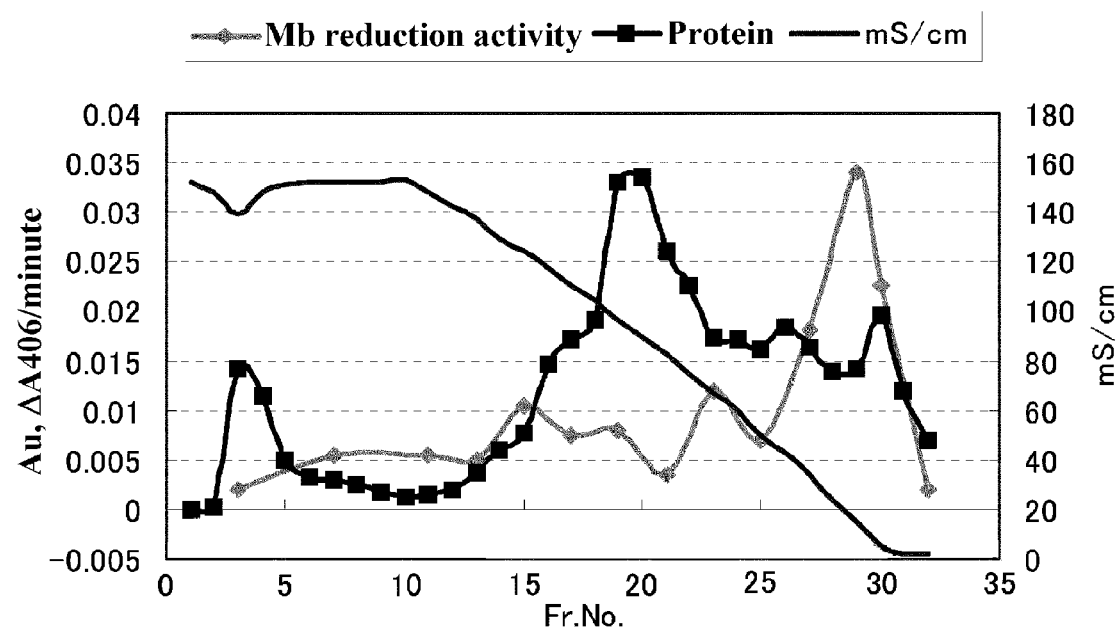
FIG. 24 shows the elution pattern and metmyoglobin reductase activity obtained by phenyl chromatography during purification of a meat color developing enzyme other than DLD.

10 mL of the first half fraction of DEAE (DEAE. Fr. No. 27-35 shown in FIG. 4) was subjected to phenyl chromatography under the following conditions (phenyl column (Hi-Trap™ Phenyl HP (5 mL); GE Healthcare)). The elution pattern and metmyoglobin reductase activity obtained by the phenyl chromatography are shown in FIG. 24. Of these fractions, the phenyl. Fr. No. 26-31 with the highest activity were dialyzed with 5 mM KPB (pH 6), and subjected to hydroxyapatite chromatography.

Figure 25:
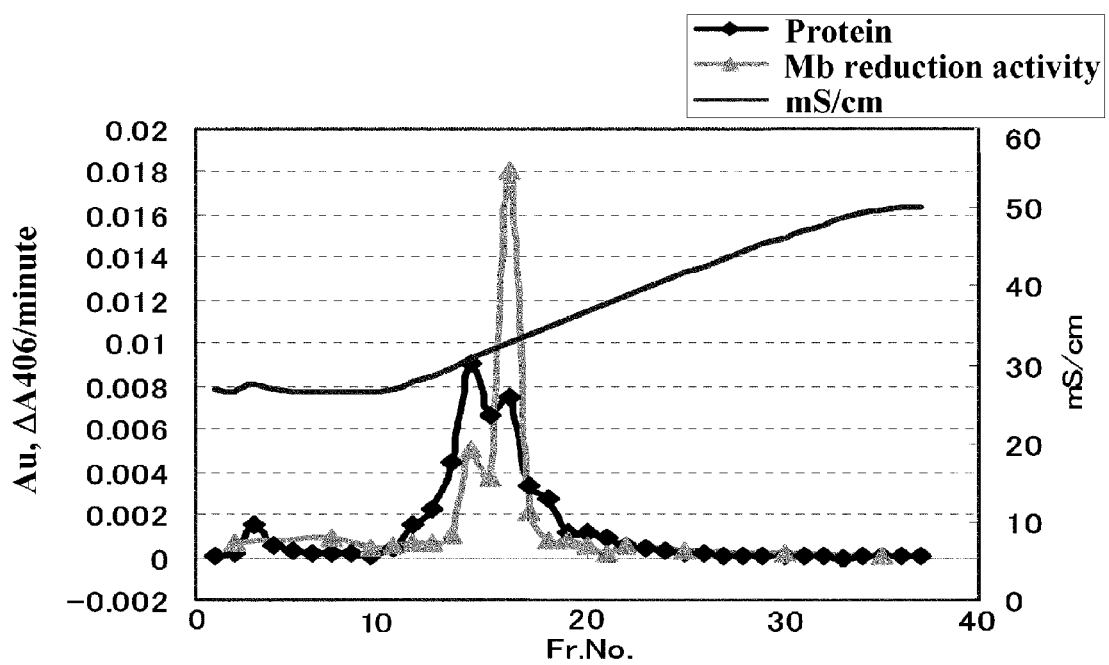
FIG. 25 shows the elution pattern and metmyoglobin reductase activity obtained by hydroxyapatite chromatography during purification of a meat color developing enzyme other than DLD.

(Phenyl Chromatography Conditions)
Carrier: Phenyl HP (5 mL)
Sample: DEAE first half Fr. (100210) UF 10 mL
Buf A: 20 mM KPB, 30% saturated ammonium sulfate (pH 6)
Buf B: 20 mM KPB (pH 6)
Flow rate: 5 mL/minute
Fraction: 5 mL
Program: (1) Buf A washing 5 cv, (2) Buf B gradient 100%/20 cv, (3) Buf B 100% washing 5 cv The phenyl. Fr. No. 26-31 obtained by the above-described phenyl chromatography were subjected to hydroxyapatite chromatography under the following conditions. FIG. 25 shows the elution pattern and metmyoglobin reductase activity obtained in the hydroxyapatite chromatography.

Figure 26:
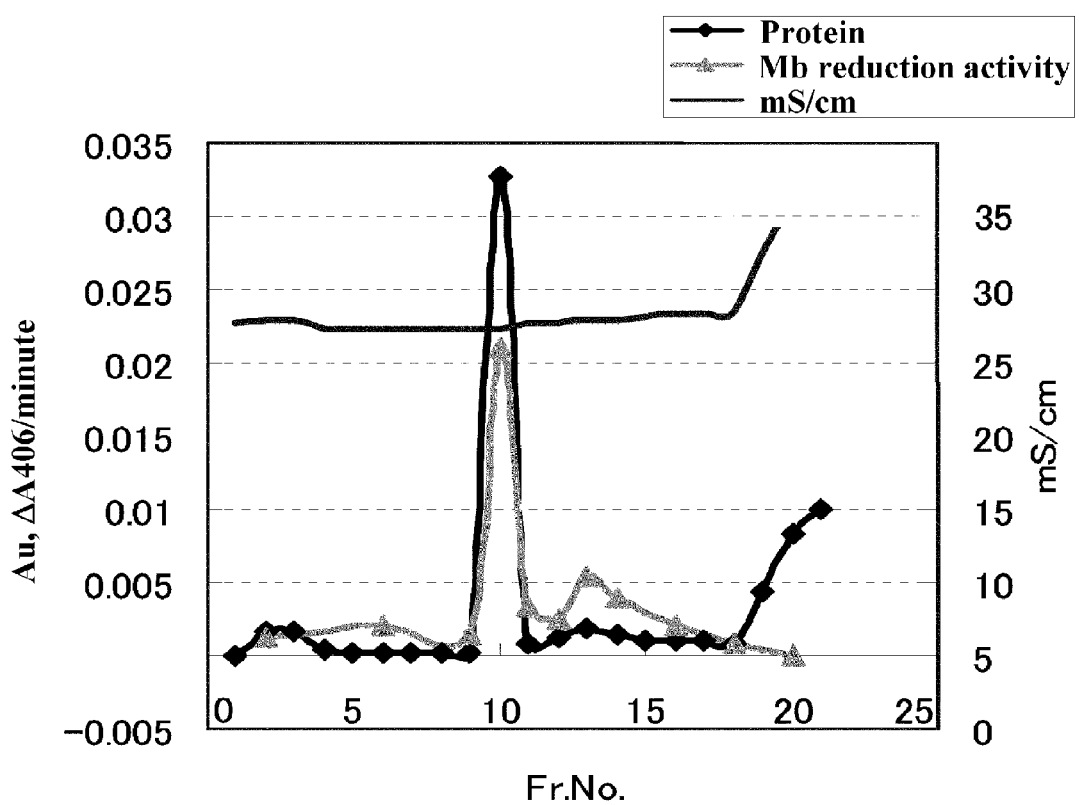
FIG. 26 shows the elution pattern and metmyoglobin reductase activity obtained by Cu affinity chromatography during purification of a meat color developing enzyme other than DLD.
Figure 27:
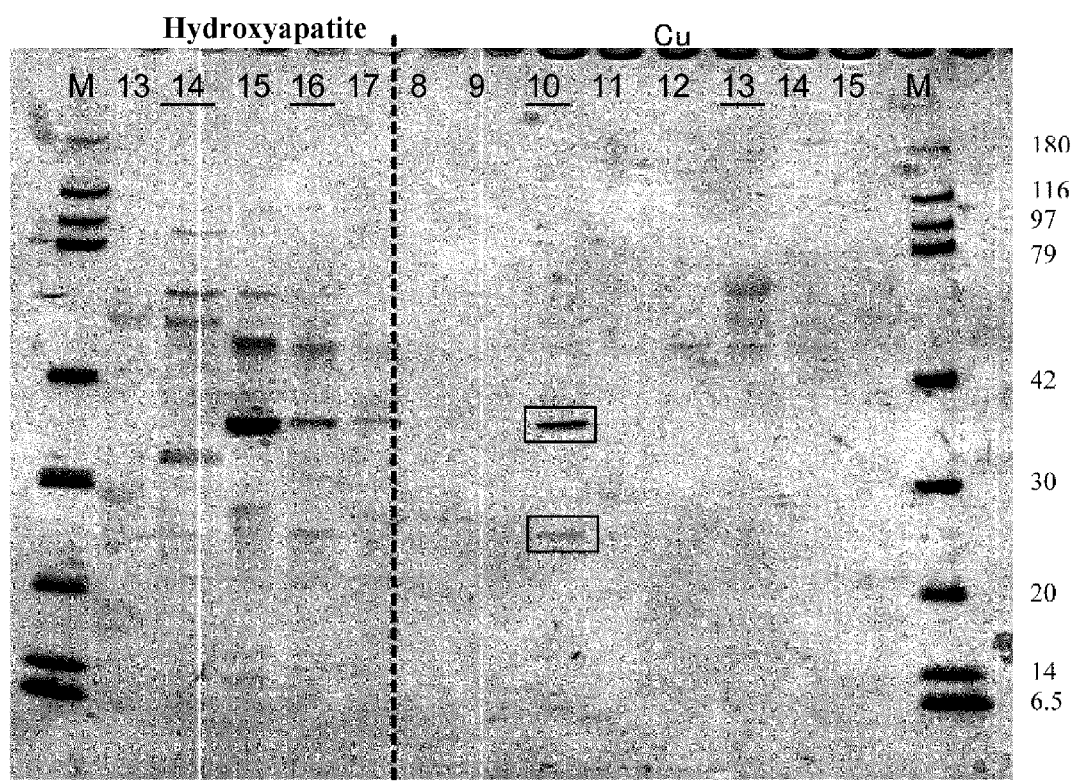
FIG. 27 shows the result of SDS-PAGE of the fractions obtained by hydroxyapatite chromatography and Cu affinity chromatography.

(Hydroxyapatite Chromatography Conditions)
Carrier: hydroxyapatite (5 mL)
Charge: phenyl purified Fr. No. 26-31
Buf A: 5 mM KPB, 0.3 M NaCl (pH 6)
Buf B: 400 mM KPB, 0.3 M NaCl (pH 6)
Flow rate: 2 mL/minute
Fraction: 5 mL
Program: (1) Buf A washing 5 cv, (2) Buf B gradient 100%/25 cv, (3) Buf B 100% 6 cv Of the fractions obtained in the hydroxyapatite chromatography, the hydroxyapatite Fr. No. 16 with the highest activity was dialyzed with 20 mM KPB and 0.3 M NaCl (pH 6), and subjected to Cu affinity chromatography under the following conditions using a Cu affinity column. FIG. 26 shows the elution pattern and metmyoglobin reductase activity obtained in the Cu affinity chromatography. Of these fractions obtained in the Cu affinity chromatography, the Cu. Fr. No. 10, 13 with the highest activity were subjected to SDS-PAGE. The results are shown in FIG. 27.

(Cu Affinity Chromatography Conditions)
Carrier: Cu2+ HP (1 mL)
Charge: hydroxyapatite-Fr. 16
Buf A: 20 mM KPB, 0.3 M NaCl (pH 6)
Buf B: 20 mM KPB, 0.3 M NaCl, 0.4 M imidazole (pH 6)
Flow rate: 1 mL/minute
Fraction: 2 mL
Program: (1) Buf A washing 6 cv, (2) Buf B gradient 10%/20 cv, (3) Buf B washing 10 cv FIG. 27 shows the result of SDS-PAGE on the hydroxyapatite Fr. No. 13-17 obtained in the hydroxyapatite chromatography, and the Cu. Fr. No. 8-15 obtained in the Cu affinity chromatography. Of these fractions, the Cu. Fr. No. 10 obtained in Cu affinity chromatography showed two main bands. The fraction was subjected to the N-terminal amino acid sequence analysis by the above-described method; the protein with a higher molecular weight was MGN-TRKKVSVI (SEQ ID NO: 8), and the protein with a lower molecular weight was MTNTLDVLKA (SEQ ID NO: 9). On the basis of the N-terminal amino acid sequence, the protein with a higher molecular weight was subjected to BLAST search, and found to have 100% homology with mdh (SEQ ID NO: 10) coding malate dehydrogenase (MDH). The protein with a lower molecular weight showed 100% homology with yodC (SEQ ID NO: 11) coding putative NAD(P)H nitroreductase (yodC). The amino acid sequence of yodC is shown in SEQ ID NO: 12. The Cu. Fr. No. 13 was assumed to be identical with dihydrolipoyl dehydrogenase, on the basis of its molecular weight.

16. Construction of Overexpression System of Meat Color Developing Enzymes (MDH, yodC)

Genes were obtained from Bacillus subtilis and Bacillus natto, and the overexpression system for MDH and yodC was constructed. Primers were made from the gene information of Bacillus subtilis and Bacillus natto, and subjected to PCR to cut out the genes. Using pET20b as the vector and BL21 (DE3 pLysS) as the host, 6×His-tag was added to the C-terminal of the enzymes for expression. The expression was confirmed by the following culture. The colonies of each enzyme (MDH or yodC) (+) Histag/pET20b/BL21 were taken, and cultured overnight at 30° C. under shaking at 300 rpm (preculture). A portion equivalent to 2% of the preculture solution was inoculated in 10 mL of LB/Amp culture medium, and IPTG was added to give the final concentration of 0.5 mM when the OD reached about 0.5 to 0.7, and cultured for 4 hours at 37° C. under shaking at 300 rpm (main culture). The bacterial cells thus obtained were collected, and suspended in 50 mM Tris-HCl (pH=7.0). The suspension was subjected to bead crushing, centrifuged, and the supernatant was used as the sample.

Figure 28:
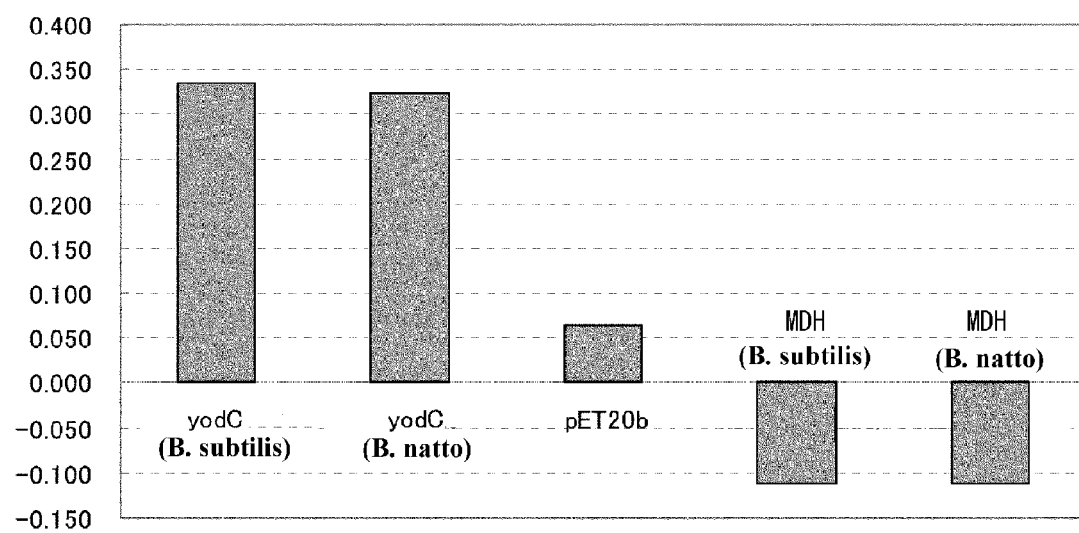
FIG. 28 shows the activities of recombinant malate dehydrogenase (MDH) and recombinant nitroreductase (Putative NAD(P)H nitroreductase: yodC). From left to right in this order, yodC/pET20b/BL21 (DE3pLysS) (*Bacillus subtilis*), yodC/pET20b/BL21 (DE3pLysS) (*Bacillus natto*), pET20b/BL21 (DE3pLysS) (empty vector), MDH/pET20b/BL21 (DE3pLysS) (*Bacillus subtilis*), and MDH/pET20b/BL21 (DE3pLysS) (*Bacillus natto*).
Figure 29:
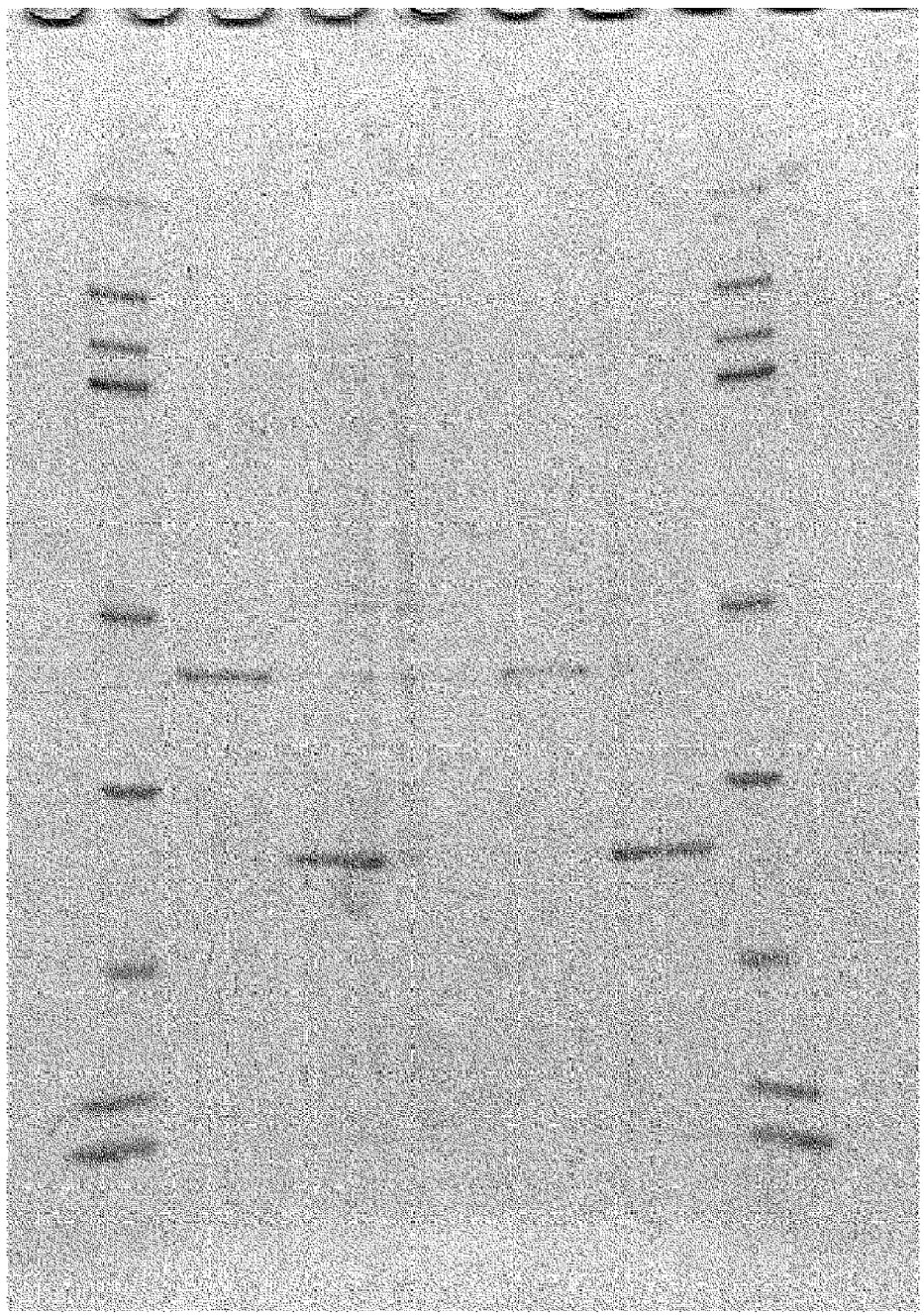
FIG. 29 shows the result of SDS-PAGE of recombinant MDH and recombinant yodC. From left to right in this order, marker, MDH/pET20b/BL21 (DE3pLysS) (*Bacillus subtilis*), yodC/pET20b/BL21 (DE3pLysS) (*Bacillus subtilis*), pET20b/BL21 (DE3pLysS), MDH/pET20b/BL21 (DE3pLysS) (*Bacillus natto*), yodC/pET20b/BL21 (DE3pLysS) (*Bacillus natto*), and marker.

The activity of the sample obtained above was confirmed. 150 µL of the enzyme sample was mixed with 50 µL of 0.1% (w/w) metmyoglobin and 0.5 M KPB (pH=5.5), 25 µL of 1 mM NADH was added to the mixture to initiate reaction, and the change in the absorbance at A406 was monitored for 10 minutes. As shown in FIG. 28, the activity of yodC was confirmed, but the activity of MDH was not found. Therefore, in order to confirm the presence or absence of expression, bands were observed by SDS-PAGE (FIG. 29). Thick bands were found at the corresponding size for both MDH and yodC.

17. Color Development Test on Purified Meat Color Developing Enzymes (MDH, yodC)

The recombinant yodC (Bacillus subtilis) and MDH (Bacillus subtilis) obtained by the above-described method were purified by Ni-Sepharose column under the following conditions, and dialyzed by 20 mM KPB (pH 6). The dialyzed sample was freeze-dried, and the enzyme powders of the recombinant yodC and MDH were obtained.

Figure 30:
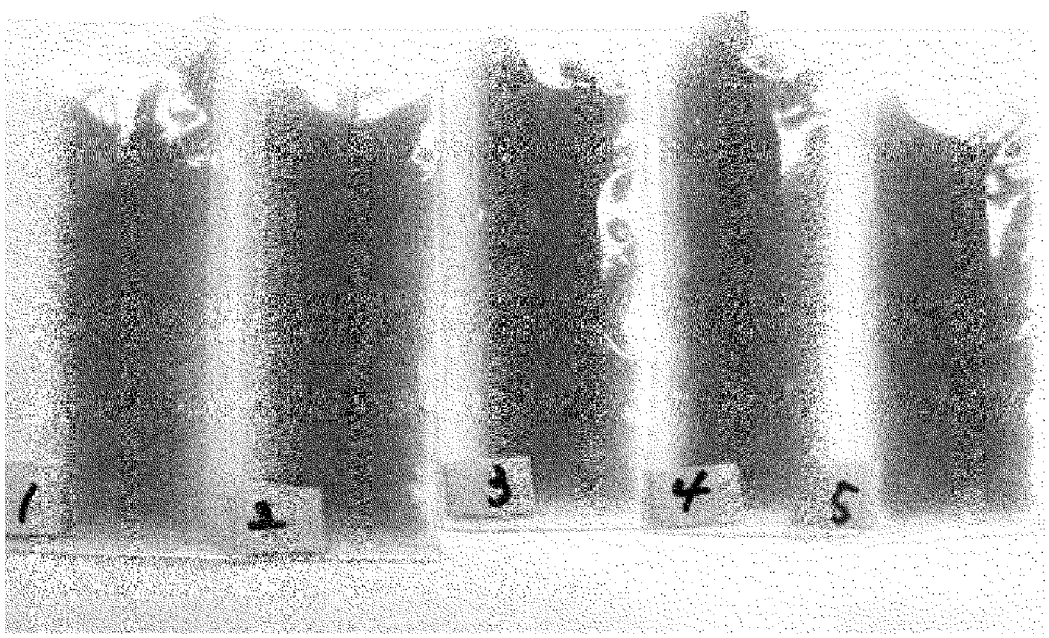
FIG. 30 shows the result of meat color development test using purified recombinant yodC and recombinant MDH.

(Chromatography Conditions)
Carrier: Ni Sepharose (25 mL)
Sample: crushed supernatant about 20 mL
Bind Buf: 20 mM KPB, 0.3 M NaCl (pH6)
Elute Buf: 20 mM KPB, 0.3 M NaCl, 0.4 M imidazole (pH6)
Flow rate: charge: 5 mL/minute, other: 10 mL/minute
Fraction: 10 mL
Program: (1) Bind Buf washing 6 cv, (2) Elute Buf 10% washing 10 cv, (3) Elute Buf 100%/20 cv gradient, (4) Elute Buf washing 10 cv Using the enzyme powders thus obtained, meat color development test was carried out. In the meat color development test, 2 g of minced pork was mixed with 37.5 µL of 40 mg/mL (4%) of myoglobin (SIGMA), 37.5 µL of 0.5 M KPB (pH=5.5), 37.5 μL of 20 mM NADH, and sample ((1) control (without addition), (2) yodC (16 mg=20 U), (3) boiled yodC, (4) MDH (16 mg), (5) boiled MDH), and allowed to react at 4° C. overnight. In order to confirm deactivation by heat treatment (100° C., 30 minutes), the samples (3) and (5) were provided. The results are shown in FIG. 30. Meat color development effect was found in yodC, but not found in MDH.

18. Study of Enzymological Properties of yodC

Figure 31:
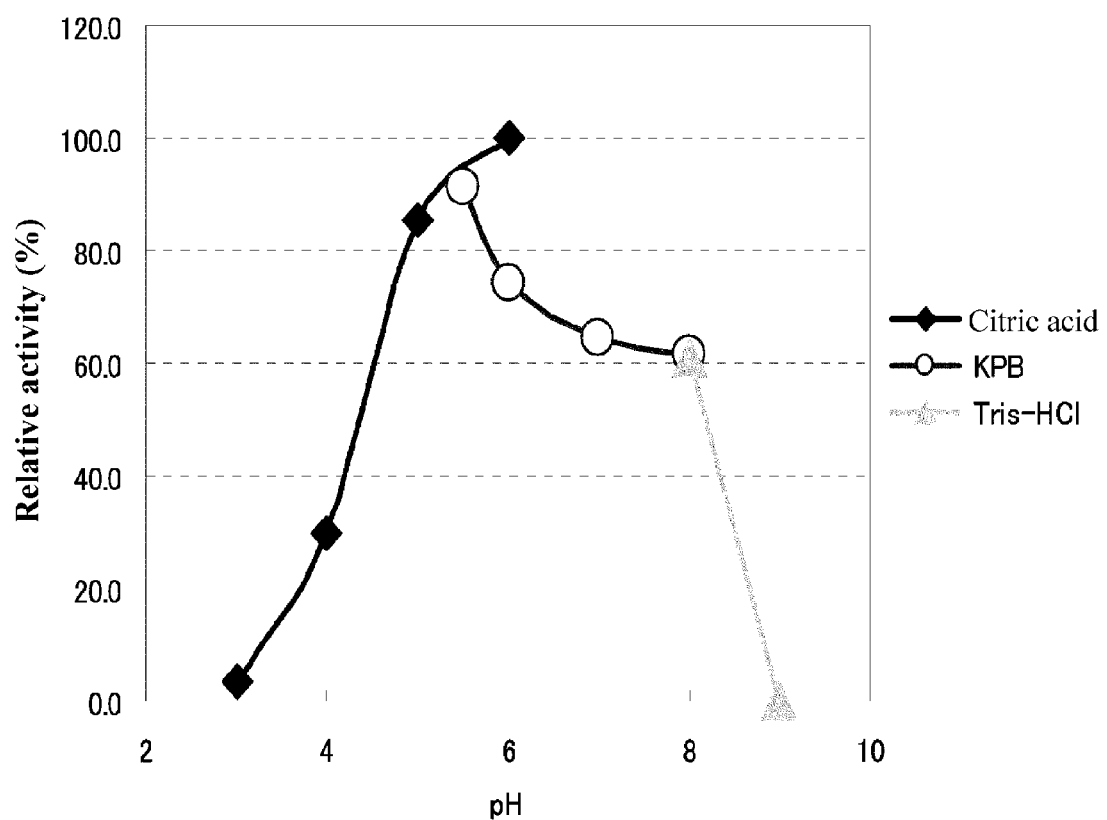
FIG. 31 shows the optimal pH of recombinant yodC.
Figure 32:
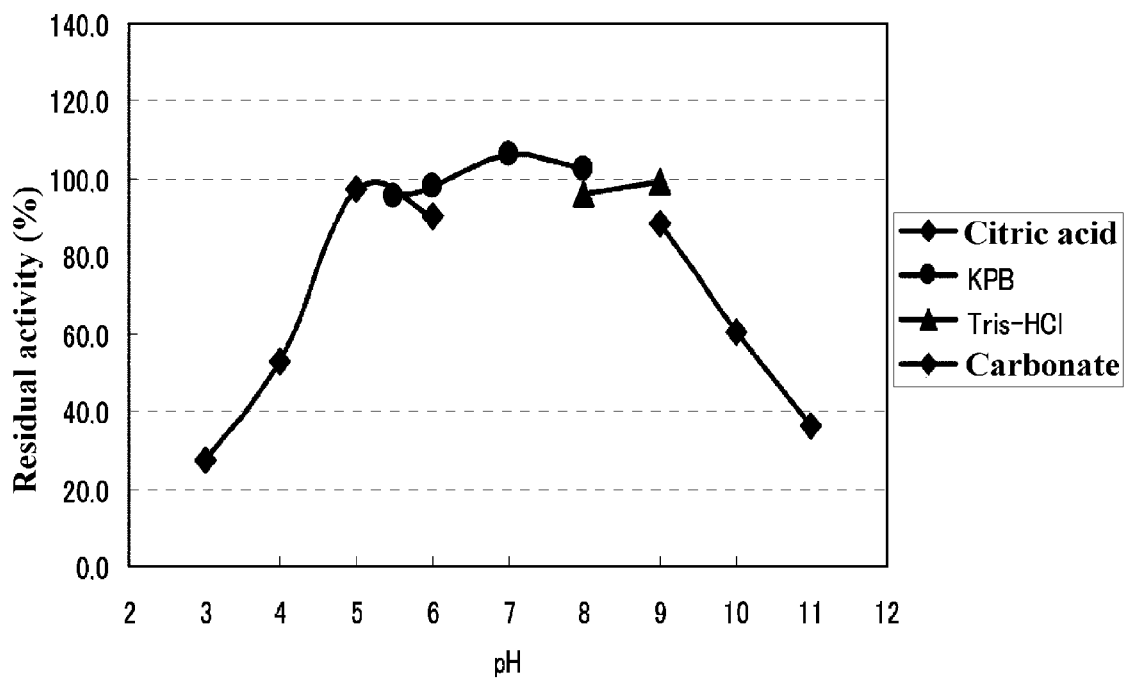
FIG. 32 shows the pH stability of recombinant yodC.
Figure 33:
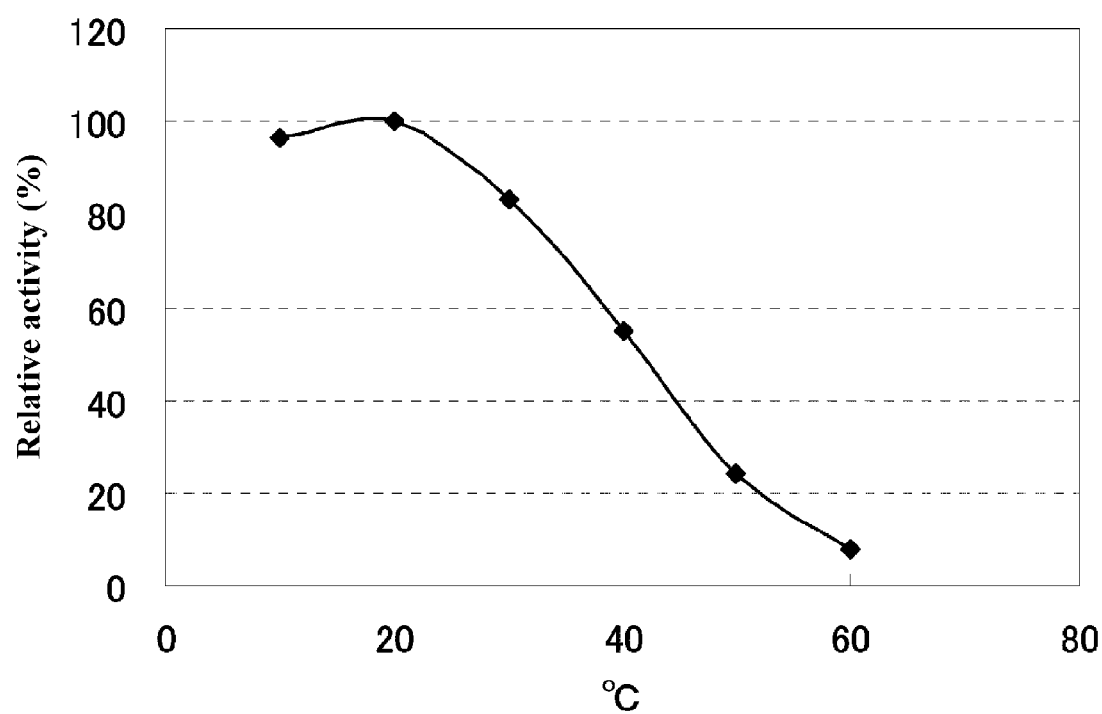
FIG. 33 shows the optimal temperature of recombinant yodC.
Figure 34:
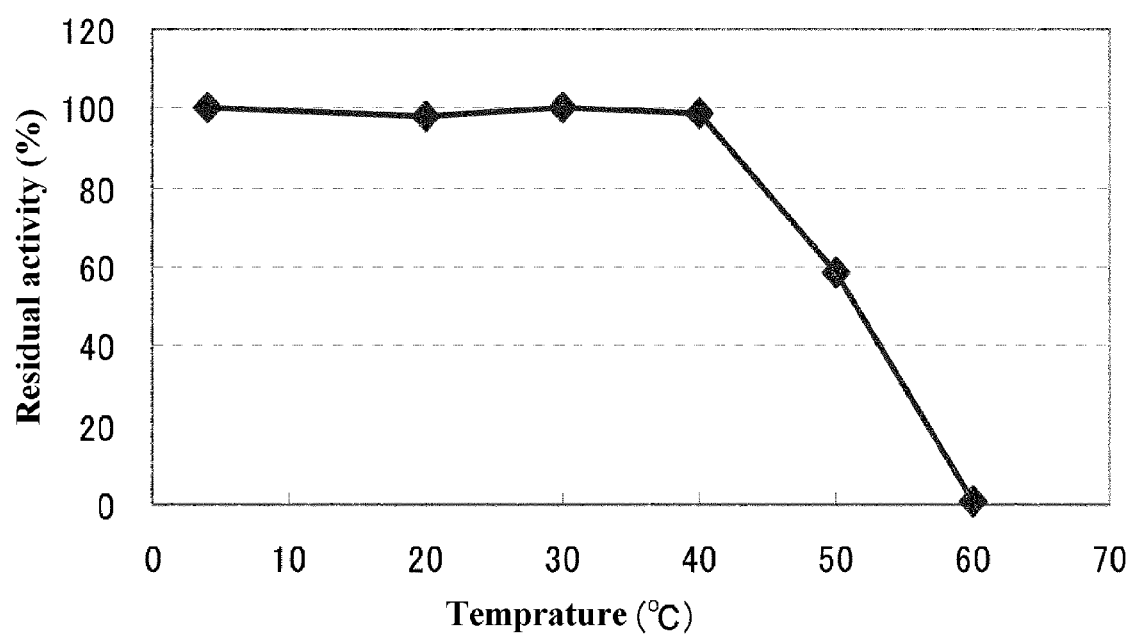
FIG. 34 shows the thermal stability of recombinant yodC.
Figure 35:
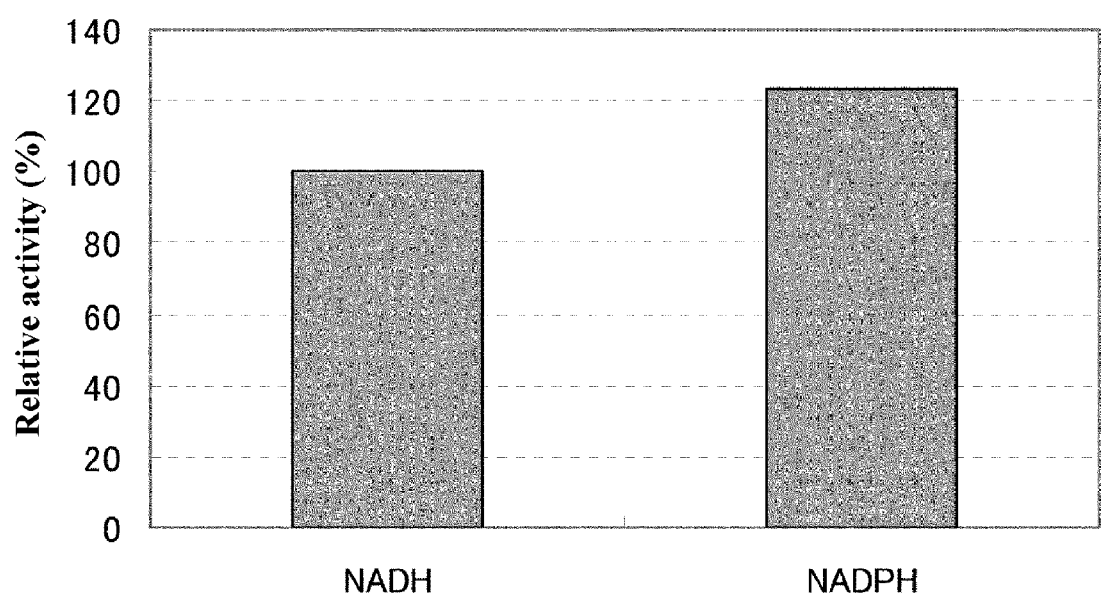
FIG. 35 shows the reactivity of recombinant yodC to NADPH.
Figure 36:
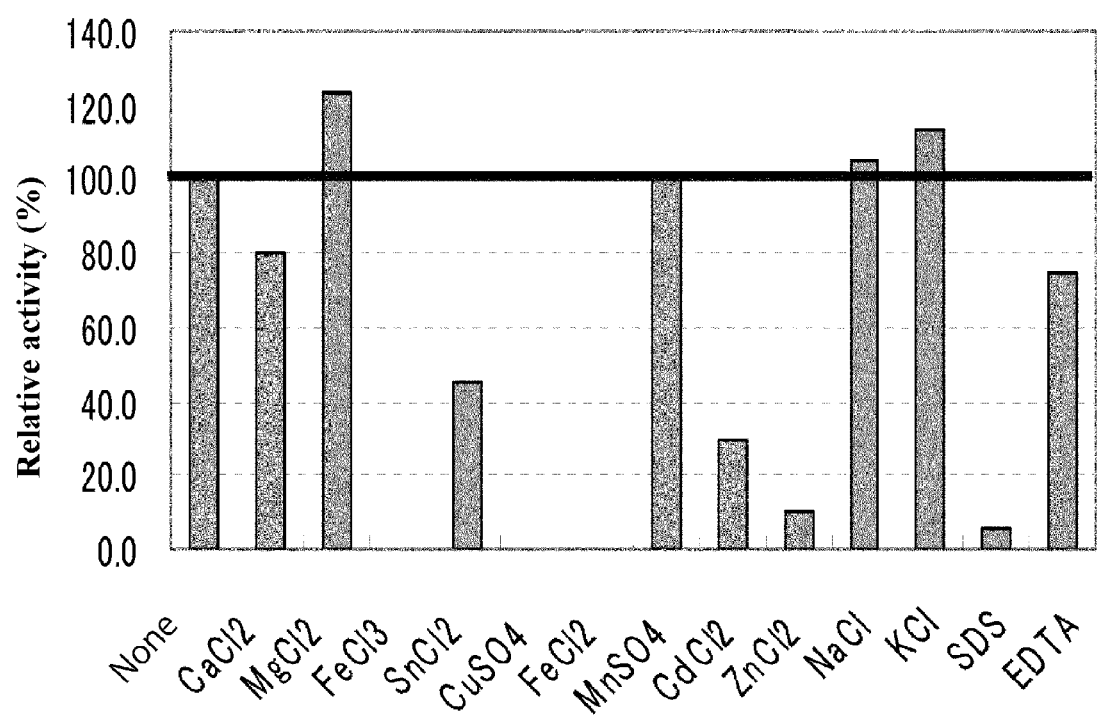
FIG. 36 shows the influences of various cations on the activity of recombinant yodC.

The enzymological properties of yodC were studied. In the same manner for DLD, the optimal pH (FIG. 31), pH stability (FIG. 32), optimal temperature (FIG. 33), thermal stability (FIG. 34), reactivity for NADPH (FIG. 35), and the influence of the metal salt (metal cation) on activity (FIG. 36) were studied. The optimal pH is in the vicinity of pH 6.0 as is the case with DLD, so that the application to meat will offer no problem. In addition, yodC was stable over a wide pH range. Regarding the optimal temperature, yodC favorably acts at low temperatures near 20° C., so that yodC is regarded as suitable for the application to meat. Also in the heat stability test, the activity was maintained up to 40° C. In the coenzyme specificity test, higher activity was achieved in the case using NADPH than the case using NADH. For metal cations, improvement in enzymatic activity was found when Mg, Na, or K was added. In addition, substrate reactivity was also studied. Under the same conditions for DLD, reactivity for potassium ferricyanide, and reactivity for myoglobin were studied. The results including the data of DLD are shown in FIGS. 37 and 38. In comparison with DLD, yodC showed about 2.6 times and 22 times higher reactivity for potassium ferricyanide and myoglobin, respectively.

INDUSTRIAL APPLICABILITY

The reducing agent of the present invention is particularly useful as a color tone improver for meat or processed meat. The reducing agent of the present invention develops the color of meat without using a color development agent such as a nitrite, and thus allows the production of processed meat product with high commercial value.

The present invention will not be limited to the above-described embodiments and examples of the invention. The present invention includes various modifications which can be readily made by those skilled in the art without departing from the scope of claims.

The contents of the articles, unexamined patent publications, and patent applications specified herein are hereby incorporated herein by reference.

SEQUENCE LIST FREE TEXT

SEQ ID NO: 4: explanation of artificial arrangement: primer DLD-Nde1-FW

SEQ ID NO: 5: explanation of artificial arrangement: primer DLD-BamH1-RV

SEQ ID NO: 6: explanation of artificial arrangement: primer DLD-Nde1-FW

SEQ ID NO: 7: explanation of artificial arrangement: primer DLD-BamH1-Histag-RV

The invention claimed is:

1. A color tone improvement method, comprising subjecting meat or processed meat to the action of a color tone improver comprising a reducing agent comprising a heme reductase obtained from a microorganism, wherein the heme reductase is nitroreductase or dehydrolipoyl dehydrogenase, and
wherein the heme reductase includes the amino acid sequence of SEQ ID NO:12 or the amino acid sequence of SEQ ID NO:3.

2. The color tone improvement method according to claim 1, wherein the microorganism is selected from the group consisting of *Bacillus subtilis, Bacillus amyloliquefaciens, Bacillus natto, Bacillus thuringiensis*, and *Bacillus mycoides*.

3. The color tone improvement method according to claim 1, wherein the microorganism is *Bacillus subtilis*.

4. The color tone improvement method according to claim 1, wherein the heme reductase is recombinant protein.

5. The color tone improvement method according to claim 1, wherein the color tone improver further comprises a second enzyme which substitutes iron in the heme group of myoglobin with zinc, and wherein the second enzyme is ferrochelatase obtained from yeast or bacteria.

6. The color tone improvement method according to claim 5, wherein the color tone improver is composed of crushed bacterial cells of *Bacillus subtilis*.

7. The color tone improvement method according to claim 1, which improves at least one of the following parameters: the color tone by color development action, color development acceleration action or color fading preventive action.

8. The color tone improvement method according to claim 5, wherein the enzymes are recombinant proteins.

9. A color tone improvement method, comprising subjecting meat or processed meat to the action of a color tone improver comprising a reducing agent comprising an enzyme obtained from a microorganism, wherein the amino acid sequence of the enzyme includes the amino acid sequence of SEQ ID NO:12, or the amino acid sequence of SEQ ID NO:3.

10. A color tone improvement method, comprising subjecting meat or processed meat to the action of crushed bacterial cells of a microorganism, wherein the microorganism is selected from the group consisting of *Bacillus subtilis, Bacillus amyloliquefaciens, Bacillus* natto, *Bacillus thuringiensis*, and *Bacillus mycoides*.

11. The color tone improvement method according to claim 10, wherein the crushed bacterial cells are obtained from *Bacillus subtilis*.

* * * * *

SEQUENCE LISTING

```
<160> NUMBER OF SEQ ID NOS: 12

<210> SEQ ID NO 1
<211> LENGTH: 15
<212> TYPE: PRT
<213> ORGANISM: Bacillus subtilis

<400> SEQUENCE: 1

Val Val Gly Asp Phe Pro Ile Glu Thr Asp Thr Leu Val Ile Gly
1               5                   10                  15

<210> SEQ ID NO 2
<211> LENGTH: 1413
<212> TYPE: DNA
<213> ORGANISM: Bacillus subtilis

<400> SEQUENCE: 2
atggtagtag gagatttccc tattgaaaca gatactcttg taattggtgc gggacctggc         60
ggctatgtag ctgccatccg cgctgcacag cttggacaaa aagtaacagt cgttgaaaaa        120
gcaactcttg gaggcgtttg tctgaacgtt ggatgtatcc cttcaaaagc gctgatcaat        180
gcaggtcacc gttatgagaa tgcaaaacat tctgatgaca tgggaatcac tgctgagaat        240
gtaacagttg atttcacaaa agttcaagaa tggaaagctt ctgttgtcaa caagcttact        300
ggcggtgtag caggtcttct taaaggcaac aaagtagatg ttgtaaaagg tgaagcttac        360
tttgtagaca gcaattcagt tcgtgttatg gatgagaact ctgctcaaac atacacgttt        420
aaaaacgcaa tcattgctac tggttctcgt cctatcgaat tgccaaactt caaatatagt        480
gagcgtgtcc tgaattcaac tggcgctttg gctcttaaag aaattcctaa aaagctcgtt        540
gttatcggcg gcggatacat cggaactgaa cttggaactg cgtatgctaa cttcggtact        600
gaacttgtta ttcttgaagg cggagatgaa attcttcctg gcttcgaaaa acaaatgagt        660
```

```
tctctcgtta cacgcagact gaagaaaaaa ggcaacgttg aaatccatac aaacgcgatg    720
gctaaaggcg ttgaagaaag accagacggc gtaacagtta ctttcgaagt aaaaggcgaa    780
gaaaaaactg ttgatgctga ttacgtattg attacagtag gacgccgtcc aaacactgat    840
gagcttggtc ttgagcaagt cggtatcgaa atgacggacc gcggtatcgt gaaaactgac    900
aaacagtgcc gcacaaacgt acctaacatt tatgcaatcg gtgatatcat cgaaggaccg    960
ccgcttgctc ataaagcatc ttacgaaggt aaatcgctg cagaagctat cgctggagag    1020
cctgcagaaa tcgattacct tggtattcct gcggttgttt ctctgagcc tgaacttgca    1080 tcagttggtt acactgaagc acaggcgaaa gaagaaggtc ttgacattgt tgctgctaaa    1140
ttcccatttg cagcaaacgg ccgcgcgctt tctcttaacg aaacagacgg cttcatgaag    1200
ctgatcactc gtaaagagga cggtcttgtg atcggtgcgc aaatcgccgg agcaagtgct    1260
tctgatatga tttctgaatt aagcttagcg attgaaggcg gcatgactgc tgaagatatc    1320
gcaatgacaa ttcacgctca cccaacattg ggcgaaatca caatggaagc tgctgaagtg    1380
gcaatcggaa gtccgattca catcgtaaaa taa                                 1413
```

<210> SEQ ID NO 3
<211> LENGTH: 470
<212> TYPE: PRT
<213> ORGANISM: Bacillus subtilis

<400> SEQUENCE: 3

```
Met Val Val Gly Asp Phe Pro Ile Glu Thr Asp Thr Leu Val Ile Gly
1               5                   10                  15

Ala Gly Pro Gly Gly Tyr Val Ala Ala Ile Arg Ala Ala Gln Leu Gly
            20                  25                  30

Gln Lys Val Thr Val Val Glu Lys Ala Thr Leu Gly Gly Val Cys Leu
        35                  40                  45

Asn Val Gly Cys Ile Pro Ser Lys Ala Leu Ile Asn Ala Gly His Arg
    50                  55                  60

Tyr Glu Asn Ala Lys His Ser Asp Asp Met Gly Ile Thr Ala Glu Asn
65                  70                  75                  80

Val Thr Val Asp Phe Thr Lys Val Gln Glu Trp Lys Ala Ser Val Val
                85                  90                  95

Asn Lys Leu Thr Gly Gly Val Ala Gly Leu Leu Lys Gly Asn Lys Val
            100                 105                 110

Asp Val Val Lys Gly Glu Ala Tyr Phe Val Asp Ser Asn Ser Val Arg
        115                 120                 125

Val Met Asp Glu Asn Ser Ala Gln Thr Tyr Thr Phe Lys Asn Ala Ile
    130                 135                 140

Ile Ala Thr Gly Ser Arg Pro Ile Glu Leu Pro Asn Phe Lys Tyr Ser
145                 150                 155                 160

Glu Arg Val Leu Asn Ser Thr Gly Ala Leu Ala Leu Lys Glu Ile Pro
                165                 170                 175

Lys Lys Leu Val Val Ile Gly Gly Gly Tyr Ile Gly Thr Glu Leu Gly
            180                 185                 190

Thr Ala Tyr Ala Asn Phe Gly Thr Glu Leu Val Ile Leu Glu Gly Gly
        195                 200                 205

Asp Glu Ile Leu Pro Gly Phe Glu Lys Gln Met Ser Ser Leu Val Thr
    210                 215                 220

Arg Arg Leu Lys Lys Lys Gly Asn Val Glu Ile His Thr Asn Ala Met
225                 230                 235                 240
```

```
Ala Lys Gly Val Glu Glu Arg Pro Asp Gly Val Thr Val Thr Phe Glu
            245                 250                 255

Val Lys Gly Glu Glu Lys Thr Val Asp Ala Asp Tyr Val Leu Ile Thr
            260                 265                 270

Val Gly Arg Arg Pro Asn Thr Asp Glu Leu Gly Leu Glu Gln Val Gly
            275                 280                 285

Ile Glu Met Thr Asp Arg Gly Ile Val Lys Thr Asp Lys Gln Cys Arg
            290                 295                 300

Thr Asn Val Pro Asn Ile Tyr Ala Ile Gly Asp Ile Ile Glu Gly Pro
305                 310                 315                 320

Pro Leu Ala His Lys Ala Ser Tyr Glu Gly Lys Ile Ala Ala Glu Ala
            325                 330                 335

Ile Ala Gly Glu Pro Ala Glu Ile Asp Tyr Leu Gly Ile Pro Ala Val
            340                 345                 350

Val Phe Ser Glu Pro Glu Leu Ala Ser Val Gly Tyr Thr Glu Ala Gln
            355                 360                 365

Ala Lys Glu Glu Gly Leu Asp Ile Val Ala Ala Lys Phe Pro Phe Ala
            370                 375                 380

Ala Asn Gly Arg Ala Leu Ser Leu Asn Glu Thr Asp Gly Phe Met Lys
385                 390                 395                 400

Leu Ile Thr Arg Lys Glu Asp Gly Leu Val Ile Gly Ala Gln Ile Ala
            405                 410                 415

Gly Ala Ser Ala Ser Asp Met Ile Ser Glu Leu Ser Leu Ala Ile Glu
            420                 425                 430

Gly Gly Met Thr Ala Glu Asp Ile Ala Met Thr Ile His Ala His Pro
            435                 440                 445

Thr Leu Gly Glu Ile Thr Met Glu Ala Ala Val Ala Ile Gly Ser
            450                 455                 460

Pro Ile His Ile Val Lys
465                 470

<210> SEQ ID NO 4
<211> LENGTH: 24
<212> TYPE: DNA
<213> ORGANISM: Artificial Sequence
<220> FEATURE:
<223> OTHER INFORMATION: primer DLD-Nde1-FW

<400> SEQUENCE: 4
ggcgtaatca tatggtagta ggag                                          24

<210> SEQ ID NO 5
<211> LENGTH: 23
<212> TYPE: DNA
<213> ORGANISM: Artificial Sequence
<220> FEATURE:
<223> OTHER INFORMATION: primer DLD-BamH1-RV

<400> SEQUENCE: 5
gataggatcc ttattttacg atg                                           23

<210> SEQ ID NO 6
<211> LENGTH: 24
<212> TYPE: DNA
<213> ORGANISM: Artificial Sequence
<220> FEATURE:
<223> OTHER INFORMATION: primer DLD-Nde1-FW

<400> SEQUENCE: 6
```

-continued

```
ggcgtaatca tatggtagta ggag                                          24
```

<210> SEQ ID NO 7
<211> LENGTH: 41
<212> TYPE: DNA
<213> ORGANISM: Artificial Sequence
<220> FEATURE:
<223> OTHER INFORMATION: primer DLD-BamH1-Histag-RV

<400> SEQUENCE: 7

```
gataggatcc ttagtggtgg tggtggtggt gttttacgat g                       41
```

<210> SEQ ID NO 8
<211> LENGTH: 11
<212> TYPE: PRT
<213> ORGANISM: Bacillus subtilis

<400> SEQUENCE: 8

Met Gly Asn Thr Arg Lys Lys Val Ser Val Ile
1               5                   10

<210> SEQ ID NO 9
<211> LENGTH: 10
<212> TYPE: PRT
<213> ORGANISM: Bacillus subtilis

<400> SEQUENCE: 9

Met Thr Asn Thr Leu Asp Val Leu Lys Ala
1               5                   10

<210> SEQ ID NO 10
<211> LENGTH: 939
<212> TYPE: DNA
<213> ORGANISM: Bacillus subtilis

<400> SEQUENCE: 10

```
atgggaaata ctcgtaaaaa agtttctgtt atcggagcag gttttaccgg agctacaact    60
gcatttttaa tcgctcaaaa agagctggca gacgttgttc ttgttgacat tccgcaattg   120
gagaacccga caagggaaa agcgcttgat atgcttgaag caagcccggt tcaaggcttt   180
gacgcaaaaa ttacgggaac atccaattac gaggatacag ccggctctga cattgttgtc   240
attacagccg gtatcgcaag aaaacctggt atgagcagag atgatctggt ctctacaaac   300
gaaaagatta tgagaagcgt tacgcaggaa atcgtgaaat attctcctga ctctattatt   360
gtggtgctga caaatcctgt tgatgcaatg acatacgcgg tgtacaaaga atcaggcttc   420
cctaaagagc gtgtaatcgg ccagtcaggt gtgcttgata cggcaagatt cagaacattt   480
gtggcagagg aattaaacct gtcagtgaaa gatgtgactg tttcgtact cggcggacac   540
ggtgacgata tggttccgct tgtgcgttat tcttatgctg gcggtatccc gcttgaaact   600
cttattccga agaacggat tgacgcaatt gtggagcgca ctagaaaagg cggaggcgaa   660
atcgtgaatc ttcttggaaa cggaagcgcg tattatgcgc ctgcggcttc tctgacagaa   720
atggtcgaag cgatcttgaa agatcagcgc cgcgtccttc ctacaattgc ttatcttgaa   780
ggggaatacg gctatgaagg catctacctt ggtgttccta caattgtagg cggcaacggt   840
cttgagcaaa tcattgaact tgaactgaca gactatgaaa gagcgcagct gaataaatca   900
gttgaatctg tcaaaaatgt catgaaagta ttatcctaa                          939
```

<210> SEQ ID NO 11

```
<211> LENGTH: 609
<212> TYPE: DNA
<213> ORGANISM: Bacillus subtilis

<400> SEQUENCE: 11
atgacgaata ctctggatgt tttaaaagca cgtgcatctg taaaggaata tgatacaaat      60
gccccgatct ctaaggagga gctgactgag ctattagacc ttgccactaa agcgccttct     120
gcttggaacc ttcagcattg gcattttaca gtattccaca gcgatgaatc aaaagcggag     180
cttcttcctg tagcgtataa tcaaaaacaa atcgttgagt cttctgctgt tgttgccatt     240
ttaggcgatt taaaggcaaa tgaaacggt gaagaagttt atgctgaatt agcaagccaa     300
ggctatatta cggatgaaat caaacaaaca ttgctcggcc aaatcaacgg tgcttaccaa     360
agcgagcaat tcgcacgtga ttccgctttc ttaaatgctt ctttagctgc tatgcagctt     420
atgattgccg caaaagcaaa aggttatgac acttgcgcaa tcggcggatt taacaaagag     480
cagttccaaa agcaatttga tatcagtgag cgctatgttc cggttatgct tatttcaatc     540
ggcaaagcag tgaagcctgc gcatcaaagc aaccgtctgc cgctttcaaa agtatcaact     600
tggctgtaa                                                              609

<210> SEQ ID NO 12
<211> LENGTH: 202
<212> TYPE: PRT
<213> ORGANISM: Bacillus subtilis

<400> SEQUENCE: 12

Met Thr Asn Thr Leu Asp Val Leu Lys Ala Arg Ala Ser Val Lys Glu
1               5                   10                  15

Tyr Asp Thr Asn Ala Pro Ile Ser Lys Glu Glu Leu Thr Glu Leu Leu
            20                  25                  30

Asp Leu Ala Thr Lys Ala Pro Ser Ala Trp Asn Leu Gln His Trp His
        35                  40                  45

Phe Thr Val Phe His Ser Asp Glu Ser Lys Ala Glu Leu Leu Pro Val
    50                  55                  60

Ala Tyr Asn Gln Lys Gln Ile Val Glu Ser Ser Ala Val Val Ala Ile
65                  70                  75                  80

Leu Gly Asp Leu Lys Ala Asn Glu Asn Gly Glu Val Tyr Ala Glu
                85                  90                  95

Leu Ala Ser Gln Gly Tyr Ile Thr Asp Glu Ile Lys Gln Thr Leu Leu
            100                 105                 110

Gly Gln Ile Asn Gly Ala Tyr Gln Ser Glu Gln Phe Ala Arg Asp Ser
        115                 120                 125

Ala Phe Leu Asn Ala Ser Leu Ala Ala Met Gln Leu Met Ile Ala Ala
    130                 135                 140

Lys Ala Lys Gly Tyr Asp Thr Cys Ala Ile Gly Gly Phe Asn Lys Glu
145                 150                 155                 160

Gln Phe Gln Lys Gln Phe Asp Ile Ser Glu Arg Tyr Val Pro Val Met
                165                 170                 175

Leu Ile Ser Ile Gly Lys Ala Val Lys Pro Ala His Gln Ser Asn Arg
            180                 185                 190

Leu Pro Leu Ser Lys Val Ser Thr Trp Leu
        195                 200
```